United States Patent
Gu

(10) Patent No.: US 10,952,958 B2
(45) Date of Patent: Mar. 23, 2021

(54) DONEZIL PAMOATE, METHOD OF PREPARATION AND USE THEREOF

(71) Applicant: Zi-Qiang Gu, Reston, VA (US)

(72) Inventor: Zi-Qiang Gu, Reston, VA (US)

( * ) Notice: Subject to any disclaimer, the term of this patent is extended or adjusted under 35 U.S.C. 154(b) by 0 days.

(21) Appl. No.: 16/669,679

(22) Filed: Oct. 31, 2019

(65) Prior Publication Data

US 2020/0129423 A1  Apr. 30, 2020

Related U.S. Application Data

(60) Continuation of application No. 16/358,391, filed on Mar. 19, 2019, now Pat. No. 10,478,395, which is a continuation of application No. 15/793,831, filed on Oct. 25, 2017, now Pat. No. 10,272,031, which is a division of application No. 15/134,182, filed on Apr. 20, 2016, now abandoned, which is a division of application No. 14/357,283, filed as application No. PCT/CN2012/085534 on Nov. 29, 2012, now Pat. No. 9,353,059, which is a continuation-in-part of application No. PCT/CN2011/083117, filed on Nov. 29, 2011.

(51) Int. Cl.

| | |
|---|---|
| *A61K 9/19* | (2006.01) |
| *A61K 9/00* | (2006.01) |
| *A61K 31/445* | (2006.01) |
| *C07C 65/11* | (2006.01) |
| *C07C 211/38* | (2006.01) |
| *C07C 271/44* | (2006.01) |
| *C07D 211/32* | (2006.01) |
| *A61K 31/13* | (2006.01) |
| *A61K 31/27* | (2006.01) |

(52) U.S. Cl.
CPC ............ *A61K 9/0019* (2013.01); *A61K 31/13* (2013.01); *A61K 31/27* (2013.01); *A61K 31/445* (2013.01); *C07C 65/11* (2013.01); *C07C 211/38* (2013.01); *C07C 271/44* (2013.01); *C07D 211/32* (2013.01)

(58) Field of Classification Search
CPC combination set(s) only.
See application file for complete search history.

(56) References Cited

U.S. PATENT DOCUMENTS

| | | |
|---|---|---|
| 2008/0090808 A1 | 4/2008 | Volvovitz |
| 2008/0171736 A1 | 7/2008 | Gregory et al. |
| 2008/0194628 A1 | 8/2008 | Mezei et al. |
| 2011/0218216 A1 | 9/2011 | Vivek et al. |

FOREIGN PATENT DOCUMENTS

| | | |
|---|---|---|
| CN | 1204319 A | 1/1999 |
| CN | 1271251 A | 10/2000 |
| CN | 101090738 A | 12/2007 |
| CN | 101708164 A | 5/2010 |
| CN | 102552218 A | 7/2012 |
| WO | 9722584 A1 | 6/1997 |
| WO | 2005065645 A2 | 7/2005 |
| WO | 2010039381 A1 | 4/2010 |
| WO | 2013005094 A1 | 1/2013 |

OTHER PUBLICATIONS

International Search report and Written Opinion for Application No. PCT/CN2011/083117 dated Sep. 6, 2012 (11 pages).
International Search Report and Written Opinion for Application No. PCT/CN2012/085534 dated Mar. 7, 2013 (12 pages).
Berge et al., "Pharmaceutical salts." J Pharm Sci. Jan. 1977; 66(1):1-19.
Zhang et al., "In vitro and in vivo evaluation of donepezil-sustained release microparticles for the treatment of Alzheimer's disease," Biomaterials, 2007, 28(10):1882-8.
First Office Action from the State Intellectual Property Office of the People's Repubic of China for Application No. 201280058819.2 dated Feb. 2, 2015 (18 pages, English translation included).
Extended European Search Report for Application No. 12853328.8 dated Sep. 1, 2015.
Second Office Action from the State Intellectual Property Office of the People's Repubic of China for Application No. 201280058819.2 dated Dec. 3, 2015 (5 pages).
Third Office Action from the State Intellectual Property Office of the People's Repubic of China for Application No. 201280058819.2 dated Aug. 1, 2016 (9 pages).
Examination Report from the European Patent Office for Application No. 12853328.8 dated Oct. 18, 2017 (4 pages).
Examination Report from the European Patent Office for Application No. 12853328.8 dated May 18, 2017 (5 pages).

*Primary Examiner* — Heidi Reese
(74) *Attorney, Agent, or Firm* — Casimir Jones, S.C.; Lisa V. Mueller

(57) ABSTRACT

The composition containing a pamoate salt of donepezil, the method of preparation and the use thereof are disclosed.

14 Claims, 20 Drawing Sheets

DONEZIL PAMOATE, METHOD OF PREPARATION AND USE THEREOF

CROSS-REFERENCE TO RELATED APPLICATIONS

This application is a continuation of U.S. patent application Ser. No. 16/358,391, filed Oct. 25, 2017, now U.S. Pat. No. 10,478,395, which is a continuation of U.S. patent application Ser. No. 15/793,831, filed Oct. 25, 2017, now U.S. Pat. No. 10,272,031, which is a divisional of U.S. patent application Ser. No. 15/134,182, filed on Apr. 20, 2016, which is a divisional of U.S. patent application Ser. No. 14/357,283, filed on May 9, 2014, now U.S. Pat. No. 9,353,059, which is a U.S. national stage entry of International Patent Application No. PCT/CN2012/085534, filed on Nov. 29, 2012, which is a continuation-in-part of International Patent Application No. PCT/CN2011/083117, filed on Nov. 29, 2011, the entire contents of each of which are fully incorporated herein by reference.

TECHNICAL FIELD

The invention relates to pamoate salts, and more particularly, to pamoate salts of donepezil, rivastigmine and memantine, pharmaceutical compositions comprising such salts, methods of preparing such salts, and methods of treating a subject in need thereof with such salts and compositions.

BACKGROUND

Polymeric extended release systems for the treatment of dementia of the Alzheimer's type have been described. However, such extended release devices tend to be costly to manufacture and difficult to produce. In addition, they typically provide for once-daily oral administration. Thus, there still exists a need for improved methods of delivering such agents which maximize the medical benefits of the active agent, can be administered more conveniently at a dosing interval longer than 24 hours, and can be produced in a more cost effective manner The chemical structure of donepezil is:

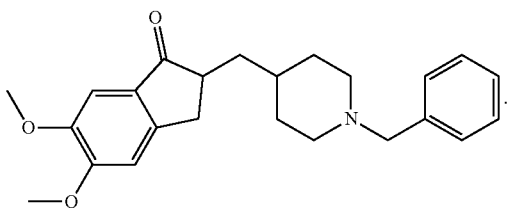 [SMILES: COc1cc2c(cc1OC)C(=O)C(CC1CCN(Cc3ccccc3)CC1)C2]

The molecular weight of donepezil is 379.49, the melting point is 207° C., and the $pK_a$ is 9.1.

Donepezil has been successfully used in the treatment of dementia (a brain disorder that affects the ability to remember, think clearly, communicate, and perform daily activities and may cause changes in mood and personality) associated with Alzheimer's disease and is currently being marketed for that purpose. Such dementia patients are often non-compliant, making it difficult to assess whether or not a patient has received the proper dosage of medication. Applicants have discovered that it can be especially desired to formulate donepezil in a depot formulation or as an intramuscular formulation to assure consistent and proper dosage of the drug substance and to maximize the clinical benefits through improved patient compliance.

Donepezil is an organic weak base. In solution, it exists as the free base form at high pH (alkaline conditions). Aqueous solubility of donepezil increases with decreasing pH of the solution due to an increasing fraction of the drug being ionized. At high concentrations of the ionized drug (protonated amine), the solubility product of the salt ($K_{sp}$) will be exceeded and the salt form will precipitate out. The nature of the drug and counterion determine the $K_{sp}$ and the associated solid state properties of the salt.

There are a wide range of counterions that have been used to prepare salts of bases using inorganic and organic acids. The most frequently used anion to form a salt of a basic drug is the hydrochloride form. For example, Aricept®, a commercial product of donepezil for oral administration, uses hydrochloride salt. Multiple organic salts of donepezil are also described in U.S. Patent Application Pub. No. 2008/0194628 by Mezei et al. These salts were prepared to improve stability, solubility or increased dissolution rate for oral administration. They possess desirable properties for immediate release dosage form. However, when extended release delivery of these salts are desired for a prolonged action, extended release technology using rate-controlling polymers are usually required as described in U.S. Patent Application Pub. No. 2011/0218216 by Vivek et al. and by P. Zhang et al, in Biomaterials (2007, 28(10):1882-8). In addition, such extended release devices tend to be costly to manufacture and difficult to produce at commercial scale. Thus, there still exists a need for improved methods of delivering such agents which maximize the medical benefits of the active agent, can be administered significantly less frequently than the current 24-hour dosing interval and can be produced in a more cost effective manner.

The chemical structure of pamoic acid is:

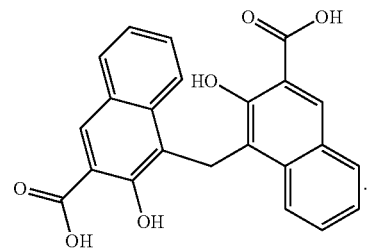 [SMILES: O=C(O)c1cc2ccccc2c(Cc2c(O)c(C(=O)O)cc3ccccc23)c1O]

The molecular weight of pamoic acid is 388 g/mol, the $pK_{a1}$ is 2.51, and $pK_{a2}$ is 3.1.

It is known that the pH of muscle tissue can vary with exercise, stress, and injury which can affect drug solubility, and thus the rate of absorption of injectable drugs. Therefore, it is desirable to find an injectable extended release formulation in which the release rate of the active ingredient is minimally dependent on pH.

SUMMARY

The present invention is directed to a variety of solid state forms, namely, pamoate salts, and more particularly, to pamoate salts of donepezil, pamoate salts of rivastigmine and pamoate salts of memantine. In addition, the present invention also relates to pharmaceutical compositions comprising such salts, methods of preparing such salts, and methods of treating a subject or patient (such as a human) in need thereof with such salts and pharmaceutical compositions. The present invention also relates to the discovery that pamoate salts of donepezil provide a desirable long acting and/or extended release profile.

In an aspect, the disclosure provides novel pamoate salts of donepezil. In some aspects, the ratio of donepezil free base to pamoic acid is 1:1 (which is referred to herein as the mono-pamoate salt of donepezil). In some embodiments, the ratio of donepezil free base (2) to pamoic acid (1) is 2:1 (which is referred to herein as the semi-pamoate salt of donepezil). In some aspects, the salt is (1) crystalline, including anhydrous, hydrate, solvate forms and their polymorphs, or (2) amorphous. The above described salts are especially useful in preparing an extended release formulation (or composition) in which the release rate is minimally dependent on the pH of the environment.

In another aspect, the present invention provides a pharmaceutical composition comprising donepezil pamoate and at least one pharmaceutically acceptable carrier. In some aspects, the carrier is a viscous aqueous or nonaqueous carrier.

In further aspect, the present invention provides a method of preparing a pamoate salt of donepezil comprising treating or mixing of donepezil with pamoic acid or treating or mixing a donepezil salt with a pamoate salt in solvent.

In another aspect, the present invention provides a method of treating a subject having dementia associated with Alzheimer's disease comprising the step of administering a therapeutically effective amount of a pharmaceutical composition comprising a pamoate salt of donepezil and at least one pharmaceutically acceptable carrier to a subject in need of treatment thereof. In some aspects, the composition is administered by injection. In some aspects, the composition is administered intramuscularly or subcutaneously.

It has been discovered that a formulation (or composition) comprising a pamoate salt of donepezil as an active ingredient or active agent, and one or more pharmaceutically acceptable carriers, can address the long felt need for a stable, pharmaceutically elegant formulation with a controllable release rate which may be useful as a depot formulation or for intramuscular or subcutaneous use.

In another aspect, the present invention relates to pamoate salts of rivastigmine. In some embodiments, the salt is (1) crystalline, including anhydrous, hydrate, solvate forms and their polymorphs, or (2) amorphous. In yet another aspect, the present invention relates to pharmaceutical compositions containing pamoate salts of rivastigmine and at least one pharmaceutically acceptable carrier. In still yet another aspect, the present invention provides a method of treating a subject having dementia associated with Alzheimer's disease comprising administering a therapeutically effective amount of a pharmaceutical composition comprising a pamoate salt of rivastigmine and at least one pharmaceutically acceptable carrier to a subject in need thereof. In some aspects, the composition is administered by injection. In some embodiments, the composition is administered intramuscularly or subcutaneously.

In still yet another aspect, the present invention relates to pamoate salts of memantine. In some embodiments, the salt is (1) crystalline, including anhydrous, hydrate, solvate forms and their polymorphs, or (2) amorphous. In yet another aspect, the present invention relates to pharmaceutical compositions containing pamoate salts of memantine and a pharmaceutically acceptable carrier. In still another aspect, In another aspect, the present invention provides a method of treating a subject having dementia associated with Alzheimer's disease comprising administering a therapeutically effective amount of a pharmaceutical composition comprising a pamoate salt of memantine and at least one pharmaceutically acceptable carrier to a patient in need thereof. In some aspects, the composition is administered by injection. In some embodiments, the composition is administered intramuscularly or subcutaneously.

DETAILED DESCRIPTION

Figure 1A:
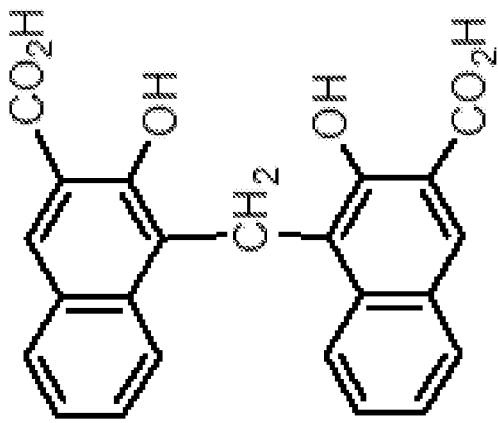
FIGS. 1A and 1B depict two salt forms of donepezil pamoate, a 1:1 and 2:1 ratio of donepezil to pamoic acid, respectively.

The present invention relates to solid state or solid forms of donepezil salts, wherein the salt is a pamoate salt. Among other advantages, pamoate salts of donepezil provide a desired long acting and/or extended release profile. Such pamoate salts of donepezil can be used to treat patients suffering from dementia, including, patients suffering from Alzheimer's disease.

Before a detailed explanation of the various aspects of the invention, it is to be understood that the invention is not limited in its application to the details of construction and the arrangement of components set forth in the following description. The invention is capable of other embodiments and of being practiced or of being carried out in various ways.

It also is specifically understood that any numerical value recited herein includes all values from the lower value to the upper value, i.e., all possible combinations of numerical values between the lowest value and the highest value enumerated are to be considered to be expressly stated in this application.

In one aspect, the invention includes pamoate salts of donepezil and compositions and formulations containing said pamoate salts. Preferably, the pamoate salt is characterized by a ratio of donepezil to pamoic acid of 1:1 or 2:1. The pamoate salt can be crystalline, anhydrous, hydrated, solvated, or amorphous.

In another aspect, the invention relates to crystalline pamoate salts of donepezil having or characterized by one or more of the following properties: (1) a powder X-ray diffraction pattern having main peaks expressed as 2-theta at about 21.1, 22.4, and 24.5±0.2 degrees 2-theta; (2) an X-ray power diffraction pattern substantially in accordance with that shown in FIG. 2; (3) a molar ratio of donepezil to pamoic acid of 1:1; and (4) combinations of (1), (2) or (3). Additionally, the crystalline pamoate salts of donepezil can further have or be characterized by the powder X-ray diffraction pattern shown in Table 1.

In yet another aspect, the invention relates to crystalline pamoate salts of donepezil having or characterized by one or more of the following properties: (1) a powder X-ray diffraction pattern having main peaks expressed as 2-theta at about 12.2, 19.2, 22.3 and 23.3±0.2 degrees 2-theta; (2) an X-ray power diffraction pattern substantially in accordance with that shown Figure; (3) a molar ratio of donepezil to pamoic acid of 2:1; and (4) combinations of (1), (2) or (3). Additionally, the crystalline pamoate salts of donepezil can further have or be characterized by the powder X-ray diffraction pattern shown in Table 2.

In yet another aspect, the invention relates to crystalline pamoate salts of donepezil having or characterized by one or more of the following properties: (1) a powder X-ray diffraction pattern having main peaks expressed as 2-theta at about 9.4, 14.8, and 17.8, 22.0 and 22.3±0.2 degrees 2-theta; (2) a molar ratio of donepezil to pamoic acid of 1:1; and (3) combinations of (1) or (2). Additionally, the crystalline pamoate salts of donepezil can further have or be characterized by the powder X-ray diffraction pattern shown in Table 3.

In yet another aspect, the present invention relates to a form of a pamoate salt of donepezil selected from the group consisting of: (1) pamoate salt of donepezil Form A (also known as the "Hydrated Form") having or characterized by a powder X-ray diffraction pattern having main peaks expressed as 2-theta at about 11.6, 12.3, 18.8, 19.3, 23.3, 24.6 and 27.3±0.2 degrees 2-theta; and (2) pamoate salt of donepezil Form B (also known as the "Anhydrous Form") having or having or characterized by a powder X-ray diffraction pattern having main peaks expressed as 2-theta at about 6.3, 11.9, 14.0, 16.2, 20.4, 21.1 and 23.7±0.2 degrees 2-theta.

Figure 12:
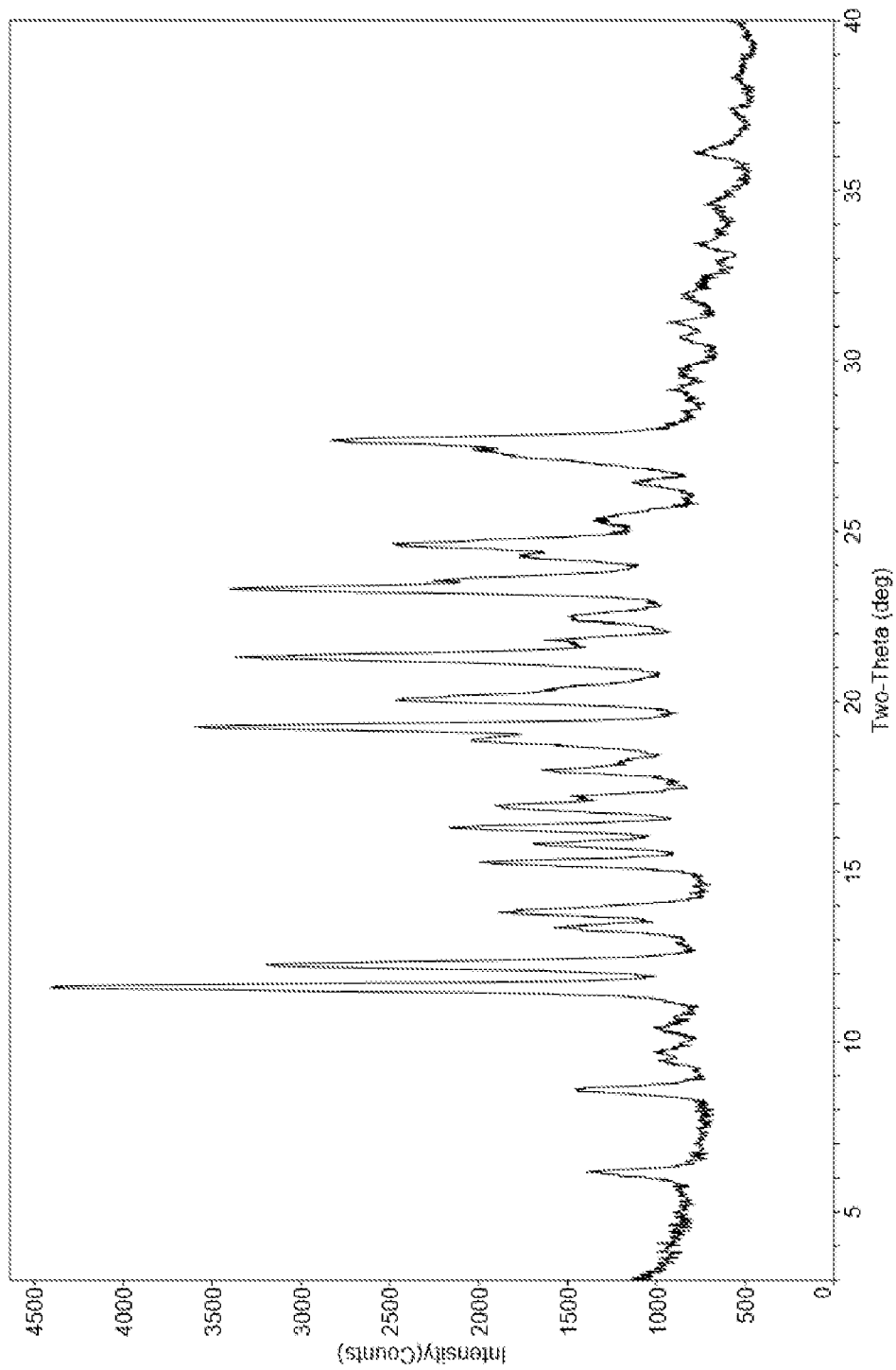
FIG. 12 depicts the X-ray powder diffraction spectrum of donepezil pamoate hydrated form as described in Example 9.

In another aspect, the present invention relates to a pamoate salt of donepzil Form A having or characterized by a powder X-ray diffraction pattern having main peaks expressed as 2-theta at about 11.6, 12.3, 18.8, 19.3, 23.3, 24.6 and 27.3±0.2 degrees 2-theta and further characterized by an x-ray diffraction pattern substantially in accordance with that shown in FIG. 12. Moreover, a pamoate salt of donepzil Form A (also known as the "Hydrated Form") can further have or be characterized by the powder X-ray diffraction pattern shown in Table 5.

Figure 13:
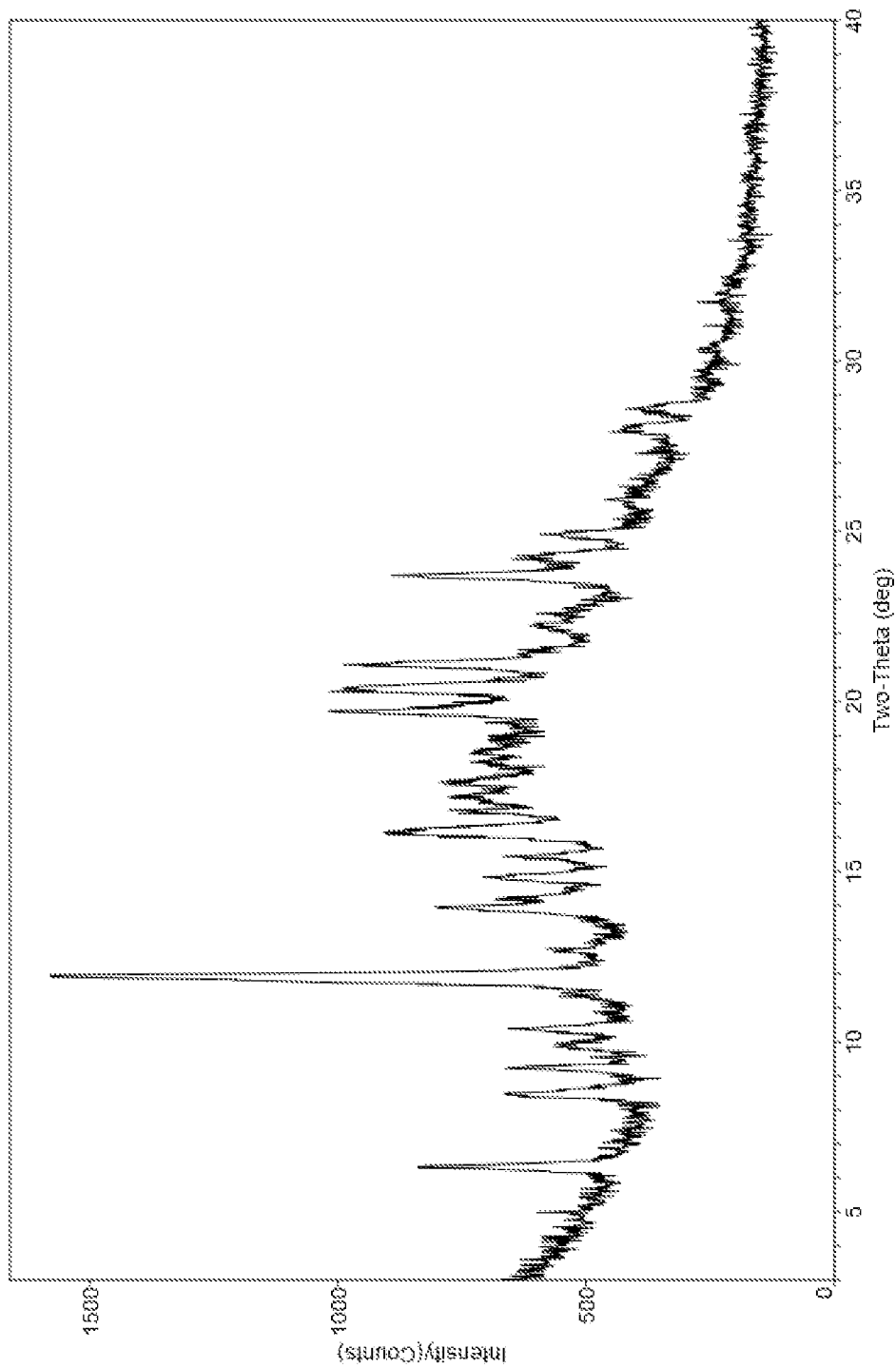
FIG. 13 depicts the X-ray powder diffraction spectrum of donepezil pamoate anhydrous form as described in Example 9.

In another aspect, the present invention relates to a pamoate salt of donepzil Form B (also known as the "Anhydrous Form") having or characterized by a powder X-ray diffraction pattern having main peaks expressed as 2-theta at about 6.3, 11.9, 14.0, 16.2, 20.4, 21.1 and 23.7±0.2 degrees 2-theta and further characterized by an x-ray diffraction pattern substantially in accordance with that shown in FIG. 13. Moreover, a pamoate salt of donepzil Form A can further have or be characterized by the powder X-ray diffraction pattern shown in Table 6.

The invention further relates to a pharmaceutical composition comprising pamoate salts of donepezil and at least one pharmaceutically acceptable carrier. In one preferred embodiment, the pharmaceutical composition is an extended release formulation comprising pamoate salts of donepezil and a polymer. In another embodiment, the pharmaceutically acceptable carrier is a viscous aqueous or nonaqueous fluid. In a preferred embodiment, the pharmaceutical composition releases an effective amount of the active agent (pamoate salt of donepezil) over a period of at least about 24 hours or at least about 48 hours. In another preferred embodiment, the active agent in the pharmaceutical composition has a duration of efficacy of at least about 7 days or at least about 14 days.

The invention further relates to methods of treating a subject, such as a warm blood mammal (such as a human patient or subject), in need of treatment thereof. The method comprises the step of administering a therapeutically effective amount of a pharmaceutical composition comprising a pamoate salt of donepezil and at least one pharmaceutically acceptable carrier.

Figure 1A:
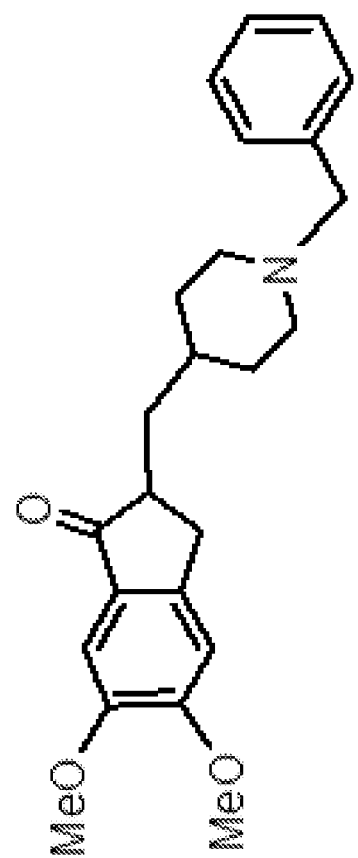
Figure 1B:
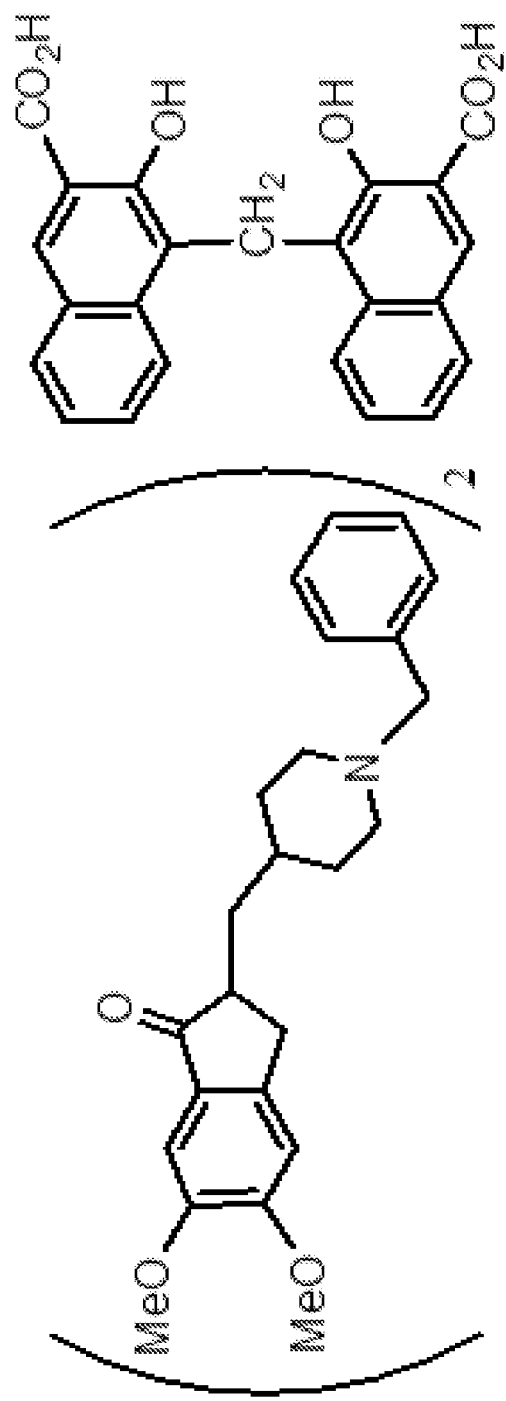

With respect to the chemical structure of pamoic acid, both carboxylic counter ions can form salt with the tertiary amine of donepezil, resulting in a ratio of donepezil to pamoic acid of 1:1 or 2:1, such as described in the FIG. 1.

It has been discovered that the pharmaceutically acceptable salts of donepezil formed using pamoic acid as a counterion surprisingly exhibit very low solubility ($K_{sp}$). This low solubility is highly desirable when used in a pharmaceutical composition to provide for extended release of the pamoate salt of donepezil when administered intramuscularly or subcutaneously. The pharmaceutical compositions of the present invention include various pharmaceutical dosage forms for purposes of administration to a subject (such as a warm blooded mammal, such as a human) in need of treatment thereof. To prepare the pharmaceutical compositions of the present invention, a pharmaceutically effective amount of one or more pamoate salts of donepezil (as the active ingredient or active agent) are combined with one or more pharmaceutically acceptable excipients. The pharmaceutically acceptable excipients used are not critical, are well known in the art, and may take a wide variety of forms depending on the form of preparation desired for administration. These pharmaceutical compositions are desirably in unitary dosage form suitable for administration.

Administration of the compositions of the present invention can be parenterally, such as by subcutaneous or intramuscular injection or implantation. For administration, the pamoate salts of donepezil can be suspended in an aqueous solvent, which may further comprise a wetting agent, such as the polyoxyethylene derivatives of sorbitan esters, e.g. polysorbate 80 (Tween® 80) and polysorbate 20 (Tween® 20), lecithin, polyoxyethylene- and polyoxypropylene ethers, sodium deoxycholate, and the like; a suspending agent such as a cellulose derivate, e.g. methylcellulose, sodium carboxymethylcellulose and hydroxypropyl methylcellulose, polyvinylpyrrolidone, alginates, chitosan, dextran, gelatin, polyethylene glycols, polyoxyethylene- and polyoxypropylene ethers and the like; an acid, e.g. hydrochloric acid, and the like; a base, e.g. sodium hydroxide, and the like; a buffer comprising a mixture of appropriate amounts of an acid such as phosphoric, succinic, tartaric, lactic, acetic, maleic or citric acid, and a base, in particular sodium hydroxide or disodium hydrogen phosphate; a preservative, e.g. benzoic acid, benzyl alcohol, butylated hydroxyanisole, butylated hydroxytoluene, chlorbutol, a gallate, a hydroxybenzoate, EDTA, phenol, chlorocresol, metacresol, benzothonium chloride, myristyl-γ-piccolinium chloride, phenylmercuri acetate, thimerosal and the like; a tonicity adjusting agent, e.g. sodium chloride, dextrose, mannitol, sorbitol, lactose, sodium sulfate, and the like. Alternatively, the pamoate salts of donepezil may be formulated in one or more oils. Appropriate oils that can be used include fixed oils, for example, peanut oil, sesame oil, cottonseed oil, corn oil, safflower oil, castor oil, ethyloleate, soybean oil, synthetic glycerol esters of long chain fatty or medium chain acids and mixtures of these and other oils. Also, thickening agents may be added to the composition, e.g. aluminum monostearate, ethylcellulose, triglycerides, hydrogenated castor oil, and the like.

In view of the usefulness of the pamoate salts of donepezil in the treatment of dementia of Alzheimer type diseases, it is evident that the present invention further provides a method of treating warm-blooded mammals (such as humans), suffering from Alzheimer's diseases. Such a method comprises the step of administering a therapeutically effective amount of a pharmaceutical acceptable composition comprising at least one pamoate salt of donepezil (also more generally referred to as the "active agent" herein) as described herein with one or more pharmaceutically acceptable excipients.

The pharmaceutically acceptable composition can be administered to a subject in need of treatment thereof as a long acting composition. In one aspect, the active agent is released from the composition over a period of at least about 24 hours, preferably about 48 hours. The active agent can also be administered in an extended release composition. In one aspect, the extended release composition releases the active agent over a period of at least about 7 days, preferably at least about 14 days, alternatively for at least 2, 3, 4, 6 or 8 weeks. The composition can be administered by injection, such as intramuscularly or subcutaneously. In one aspect, the compositions can be administered as a single or sole dose. However, the compositions described herein are particularly beneficial for those subjects in need of treatment thereof that require constant or chronic therapy, such as those subjects that receive repeated doses over several weeks or months or more. In such dosing regimens, the method can comprise the steps of: (1) administering as first dose an first extended release composition containing the pamoate salts of donepezil as described herein followed by (2) administering as a second dose (and as subsequence doses if necessary), a second extended release composition. The second extended release composition can be the same, substantially the same or different than the first extended release composition. Specifically, the second extended release composition can include as the active agent the pamoate salts of donepezil as described herein or an active agent that is other than the pamoate salts of donepezil as described herein. The second composition can be administered at about 7 days, or more, such as at least about 14 days, or at least about 17 days, after the first administration of the first extended release composition, where the first administration results in the release of active agent for a period of 1, 2, 3, 4, 5, 6, 7, 8, 9, 10, 11, 12, 13, 14 days, or more.

As used herein, the term "individual", "subject" or "patient" refers to a warm blooded animal which is afflicted with a particular disease state. Warm blooded animals include mammals, such as humans.

The term "therapeutically effective amount" is defined as an amount resulting in the improvement of any parameters or clinical symptoms. The actual dose may vary with each patient and does not necessarily indicate a total elimination of all disease symptoms. A therapeutically effective amount of the compound used in the methods described herein can be readily determined by one skilled in the art, such as an attending physician, by observing results obtained under analogous circumstances and by using conventional techniques. In determining the therapeutically effective dose, the attending physician considers a number of factors, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

Preferred amounts and modes of administration can be readily be determined by one skilled in the art depending upon the particular characteristics of the compound selected, the disease state to be treated, the stage of the disease, and other relevant circumstances using formulation technology known in the art, described for example in Remington's Pharmaceutical Sciences, latest edition, Mack Publishing Co.

Pharmaceutical compositions can be manufactured utilizing routine techniques known in the art. Typically a therapeutically effective amount of the compound (salt) will be combined with a pharmaceutically acceptable carrier.

The pharmaceutical compositions of the present invention may be administered parenterally. For instance, they can be administered by injection. Preferred methods of parenteral administration include intramuscular and subcutaneous injection.

For parenteral administration, the compounds (salt) may be dissolved in a physiologically acceptable pharmaceutical carrier and administered as either a solution or a suspension. Viscous injectable carriers are preferred, having for example, a viscosity of at least 20 cp at 20° C. In other embodiments, the fluid phase of the suspension has a viscosity at 20° C. of at least about 30 cp, 40 cp, 50 cp, and 60 cp. The composition can also comprise a viscosity enhancing agent, a density enhancing agent, a tonicity enhancing agent, and/or a wetting agent. Suitable pharmaceutical carriers include water, saline, dextrose solutions, fructose solutions, ethanol, or oils of animal, vegetative, or synthetic origin. The pharmaceutical carrier may also contain preservatives, and buffers as are known in the art.

When the composition is to be used as an injectable material, including, but not limited to, needle-less injection, it can be formulated into a conventional injectable carrier. Suitable carriers include biocompatible and pharmaceutically acceptable solutions, emulsions or suspensions.

In another embodiment, the formulation can be surgically implanted. Such formulations can include any of the well-known biodegradable and bioerodable carriers, such as polylactides, poly-lactide-co-glycolides and collagen formulations. Such materials may be in the form of solid implants, sponges, and the like. In any event, for local use of the materials, the active ingredients usually are present in the carrier or excipient in a weight ratio of from about 1:1000 to 1:20,000, but are not limited to ratios within this range.

The present invention also relates to methods of making pamoate salts of donepezil. Specifically, pamoate salts of donepezil can be prepared in a variety of different ways. For example, in one aspect, pamoate salts of donepezil can be prepared directly by treating or mixing donepezil (such as a free base) with pamoic acid in a solvent (such as water, ethanol or DMSO). In another aspect, pamoate salts of donepezil can be prepared by treating or mixing a donepezil salt (such as a hydrochloride salt) with a pamoate salt (such as disodium pamoate) in one or more solvents. For example, donepezil pamoate can be prepared by adding a solution of disodium pamoate, or other pamoate salt in an appropriate solvent, such as water, to a solution of donepezil hydrochloride and leaving the solution to stir for a period of time, such as, for example, about 3 hours, until precipitation occurs. Alternatively, other methods such as evaporation, slurry, anti-solvent, cooling and hydration can also be used to precipitate the salt.

Pamoate salts can also be formed with Rivastigmine (Exelon), Galantamine (Razadyne), Tacrine (Cognex); and Memantine (Namenda), besides Donepezil (Aricept), which are the drugs approved for the treatment of the cognitive symptoms (memory loss, confusion, and problems with thinking and reasoning) of Alzheimer's disease.

In another aspect, the present invention relates to a solid state form of a rivastigmine salt, wherein the salt is a pamoate salt. The pamoate salt can be crystalline, anhydrous, hydrated, solvated, or amorphous. In yet another aspect, the invention relates to crystalline pamoate salts of rivastigmine having or characterized by one or more of the following properties: (1) a powder X-ray diffraction pattern having main peaks expressed as 2-theta at about 9.8, 19.0, 23.0, 26.8, 36.8 and 37.0±0.2 degrees 2-theta; (2) an X-ray power diffraction pattern substantially in accordance with that shown in FIGS. 14; and (3) combinations of (1) and (2). Additionally, the crystalline pamoate salts of rivastigmine can further have or be characterized by the powder X-ray diffraction pattern shown in Table 7. In still yet another aspect, the present invention also relates to compositions containing the above described pamoate salts of rivastigmine and pharmaceutical compositions containing said compositions and at least one pharmaceutically acceptable carrier.

In still another aspect, the present invention relates to a solid state form of a memantine salt, wherein the salt is a pamoate salt. The pamoate salt can be crystalline, anhydrous, hydrated, solvated, or amorphous. In yet another aspect, the invention relates to crystalline pamoate salts of memantine having or characterized by one or more of the following properties: (1) a powder X-ray diffraction pattern having main peaks expressed as 2-theta at about 7.6, 12.7, 13.2, 18.3, 19.3 and 31.8±0.2 degrees 2-theta; (2) an X-ray power diffraction pattern substantially in accordance with that shown in FIGS. 17; and (3) combinations of (1) and (2). Additionally, the crystalline pamoate salts of memantine can further have or be characterized by the powder X-ray diffraction pattern shown in Table 8. In still yet another aspect, the present invention also relates to compositions containing the above described pamoate salts of memantine and pharmaceutical compositions containing said compositions and at least one pharmaceutically acceptable carrier.

The following examples are intended to illustrate and not to limit the scope of the present invention.

EXAMPLES

Example 1: Making Donepezil Pamoate at a 1:1 Molar Ratio of Donepezil to Pamoic Acid from DMSO/Water (Mono-Pamoate Salt of Donepezil)

796 mg of donepezil free base and 776 mg of pamoic acid were dissolved in 6 ml of DMSO and stirred for 7 hours at room temperature. 30 ml of water were added to precipitate the solids. The solids were filtered and dried at 40-60° C. to yield donepezil pamoate at a 1:1 molar ratio of donepezil to pamoic acid.

Figure 2:
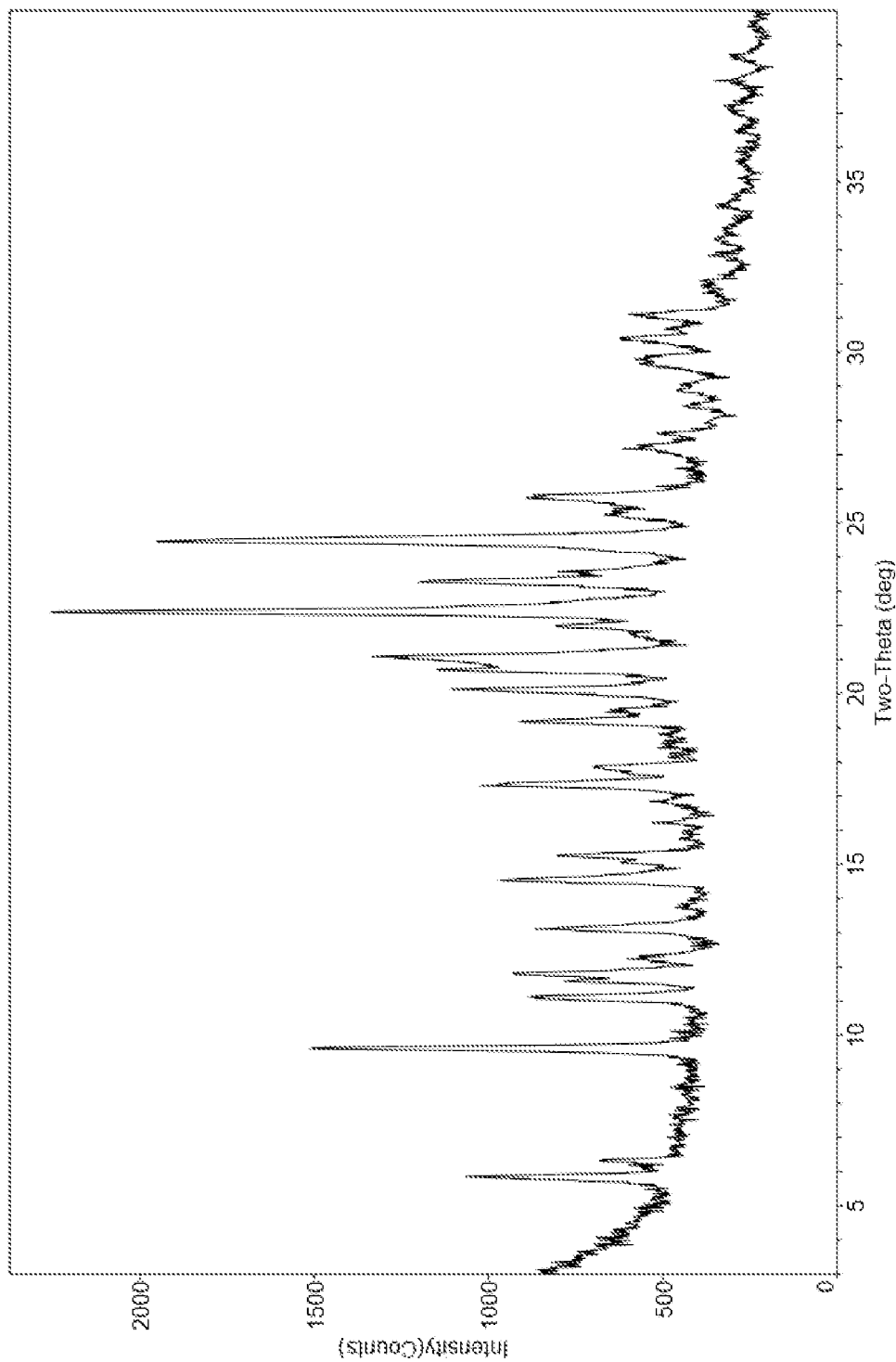
FIG. 2 depicts the x-ray powder diffraction ("XRPD") spectrum of donepezil pamoate (1:1 ratio of donepezil to pamoic acid) obtained from donepezil and pamoic acid in DMSO/water.

X-ray powder diffraction ("XRPD") patterns of above solids were obtained using a Bruker D8 Advance x-ray powder diffractometer with copper Kα radiation at a wavelength of 1.5406 Å. Instrumental conditions included a step size of 0.02°/step, a scan rate of 0.2 seconds/step, a 2-theta range of 3 to 40 degrees, a voltage of 40 kV, a current of 40 mA, and a Lynxeye detector. Samples were packed into recessed sample holders for analysis. A typical example of an x-ray diffraction pattern for an Example 1 salt is shown in FIG. 2. Table 1 sets forth the x-ray diffraction data wherein d(A) represents the interplanar spacing and I % represents the typical relative intensities. The key peaks are bolded and underlined in Table 1.

TABLE 1

| 2-Theta | d(A) | I % |
|---|---|---|
| 5.859 | 15.0711 | 33.2 |
| 6.322 | 13.968 | 12.1 |
| 9.601 | 9.2045 | 63.1 |
| 11.123 | 7.9479 | 26.8 |
| 11.582 | 7.6338 | 22.6 |
| 11.809 | 7.4881 | 30.4 |
| 12.231 | 7.2302 | 11.8 |
| 13.109 | 6.7483 | 27.5 |
| 14.538 | 6.088 | 33.1 |
| 15.262 | 5.8006 | 23 |
| 16.218 | 5.4609 | 7.8 |
| 16.843 | 5.2597 | 6.1 |
| 17.305 | 5.12 | 35.4 |
| 17.871 | 4.9593 | 14.4 |
| 19.191 | 4.6211 | 25.7 |
| 19.459 | 4.558 | 10.3 |
| 20.125 | 4.4087 | 34.4 |
| 20.698 | 4.2879 | 37.7 |
| 21.079 | 4.2112 | 47.6 |
| 21.993 | 4.0383 | 16.9 |
| 22.394 | 3.9667 | 100 |
| 23.274 | 3.8188 | 39.4 |
| 23.577 | 3.7703 | 17.5 |
| 24.455 | 3.6369 | 85.6 |
| 25.237 | 3.526 | 12.9 |
| 25.733 | 3.4592 | 26.9 |
| 27.277 | 3.2668 | 11 |
| 27.619 | 3.227 | 9.2 |
| 28.417 | 3.1382 | 6.1 |
| 28.879 | 3.0891 | 6.5 |
| 29.793 | 2.9963 | 11.2 |
| 30.405 | 2.9375 | 14.1 |
| 30.674 | 2.9122 | 7.3 |
| 31.108 | 2.8726 | 12.7 |
| 37.959 | 2.3684 | 7 |

Example 2: Making Donepezil Pamoate at a 2:1 Molar Ratio of Donepezil to Pamoic Acid from DMSO/Water System (Semi-Pamoate Salt of Donepezil)

Figure 3:
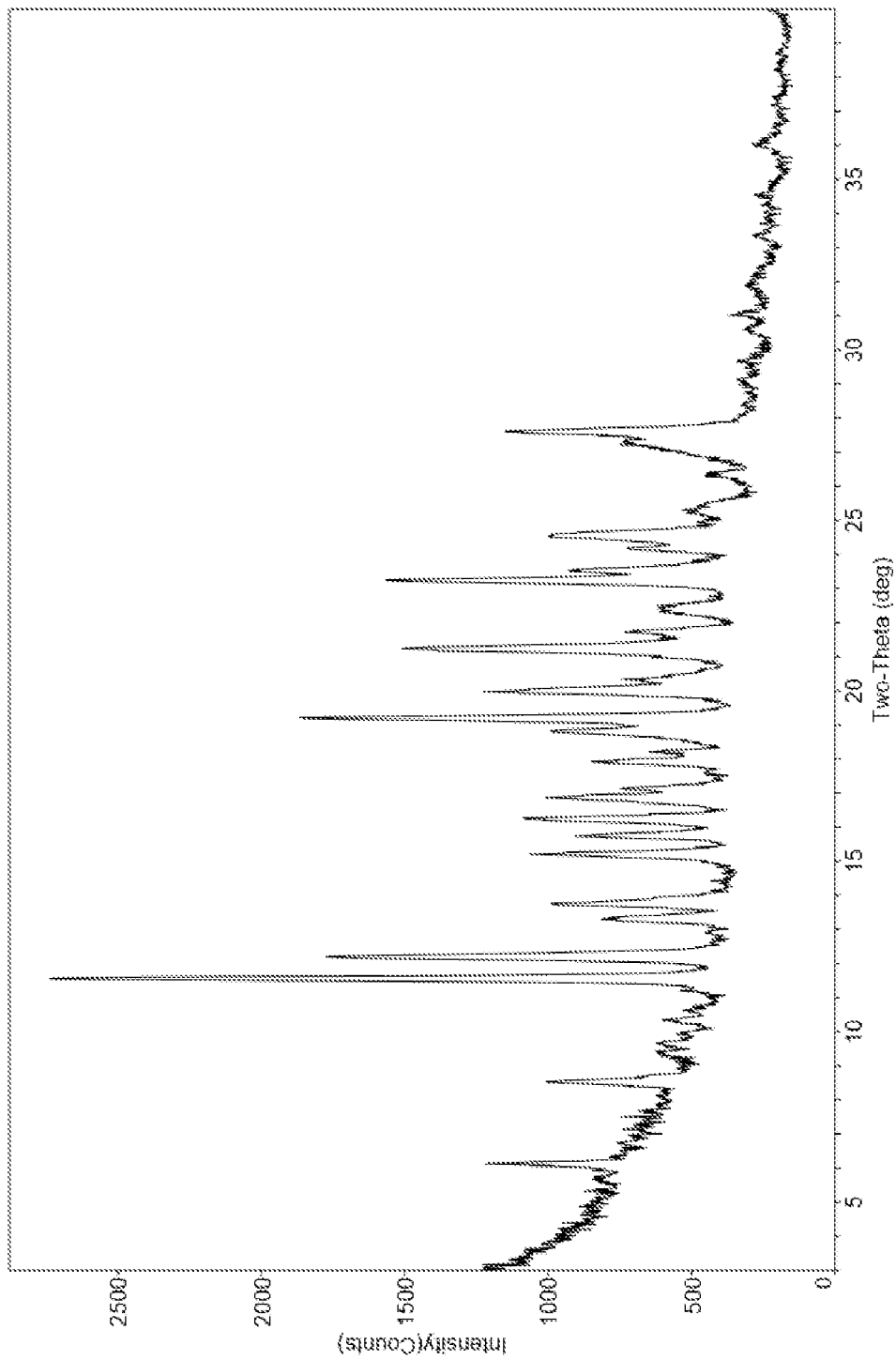
FIG. 3 depicts the XRPD spectrum of donepezil pamoate (2:1 ratio of donepezil to pamoic acid) obtained from donepezil and pamoic acid in DMSO/water.

1554 mg of donepezil free base and 776 mg of pamoic acid were dissolved in 6 ml of DMSO and stirred for 5 hours at room temperature. 30 ml of water were added to precipitate the solids. The solids were filtered and dried at 40-50° C. to yield donepezil pamoate at a 2:1 molar ratio of donepezil to pamoic acid. A typical example of an x-ray diffraction pattern for an Example 2 salt is shown in FIG. 3 and the interplanar spacing and typical relative intensities are set forth in Table 2. The key peaks are bolded and underlined in Table 2.

TABLE 2

| 2-Theta | d(A) | I % |
|---|---|---|
| 6.13 | 14.4053 | 20.8 |
| 8.53 | 10.3574 | 18.9 |
| 9.371 | 9.4302 | 5.4 |
| 9.656 | 9.1518 | 6.2 |
| 10.341 | 8.5469 | 6.5 |
| 11.562 | 7.647 | 100 |
| 12.209 | 7.2432 | 57.8 |
| 13.298 | 6.6524 | 18.3 |
| 13.754 | 6.4329 | 25.7 |
| 15.206 | 5.822 | 28.8 |
| 15.74 | 5.6255 | 21.8 |
| 16.269 | 5.4436 | 28.8 |
| 16.865 | 5.2527 | 25.6 |
| 17.132 | 5.1714 | 14.3 |
| 17.913 | 4.9478 | 18.3 |
| 18.201 | 4.87 | 9 |
| 18.81 | 4.7138 | 24.8 |
| 19.209 | 4.6168 | 63.5 |
| 19.973 | 4.4418 | 36.2 |
| 20.334 | 4.3638 | 14.9 |
| 21.25 | 4.1777 | 48.3 |
| 21.728 | 4.0868 | 15.2 |
| 22.431 | 3.9604 | 9.9 |
| 23.25 | 3.8226 | 49.7 |
| 23.52 | 3.7793 | 22 |
| 24.169 | 3.6793 | 12.8 |
| 24.531 | 3.6259 | 24.5 |
| 27.221 | 3.2733 | 18.9 |
| 27.601 | 3.2292 | 36.7 |

Example 3: Making Donepezil Pamoate at a 1:1 Molar Ratio of Donepezil to Pamoic Acid from Donepezil Hydrochloride and Disodium Pamoate in Water. (Semi-Pamoate Salt of Donepezil)

23.2 mg of donepezil hydrochloride were dissolved in 0.8 ml of water. 22.5 mg of disodium pamoate were dissolved in 2 ml of water. The disodium pamoate solution was added dropwise to the donepezil hydrochloride solution. The resulting mixture was stirred overnight at room temperature and filtered. The solids were vacuum dried at 50° C. to yield donepezil pamoate at a 1:1 molar ratio of donepezil to pamoic acid.

Figure 4:
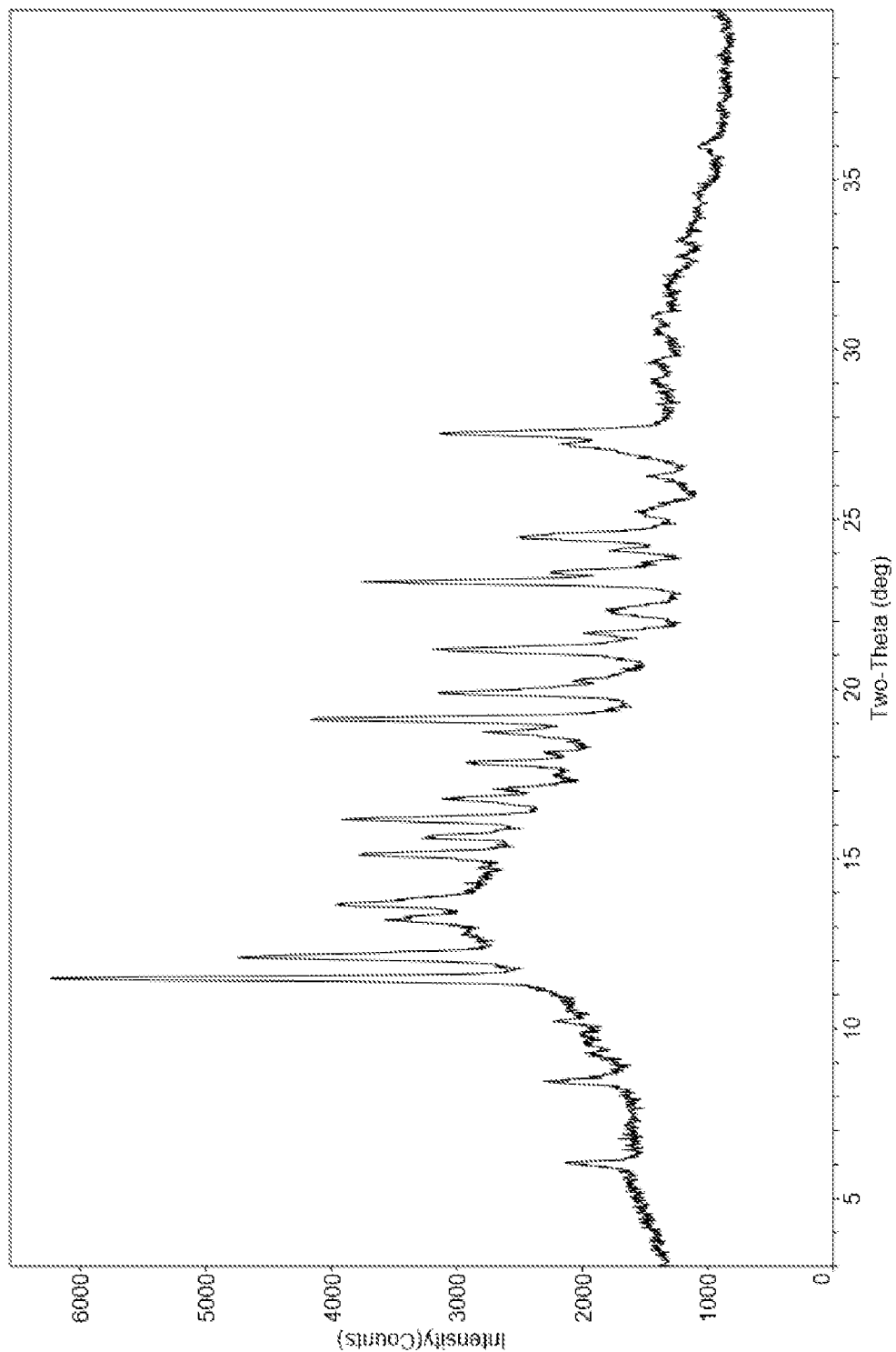
FIG. 4 depicts the XRPD spectrum of donepezil pamoate (2:1 ratio of donepezil to pamoic acid) obtained from donepezil hydrochloride and disodium pamoate in water.

The XRPD pattern of an Example 3 salt is shown in FIG. 4.

Example 4: Making Donepezil Pamoate at a 2:1 Molar Ratio of Donepezil to Pamoic Acid from Donepezil Hydrochloride and Disodium Pamoate in Water (Semi-Pamoate Salt of Donepezil)

2081 mg of donepezil hydrochloride were dissolved in 30 ml of water. 1075 mg of disodium pamoate were dissolved in 6 ml of water. The disodium pamoate solution was added dropwise to the donepezil hydrochloride solution and 40 ml of water were added to the mixed solution. The resulting mixture was stirred for 3 hours at room temperature and filtered. The solids were vacuum dried at 50° C. to yield donepezil pamoate at a 2:1 molar ratio of donepezil to pamoic acid.

Example 5: Making 1:1 Molar Ratio of Donepezil to Pamoic Acid from Donepezil Hydrochloride and Disodium Pamoate in Ethanol (Mono-Pamoate Salt of Donepezil)

23.02 mg of donepezil hydrochloride salt was dissolved in 0.8 ml of ethanol; 22.98 mg of disodium pamoate was dissolved in 2 ml of ethanol. The two ethanol solutions were combined, stirred overnight, filtered and vacuum dried at 50° C. to yield 1:1 donepezil pamoate.

Figure 5:
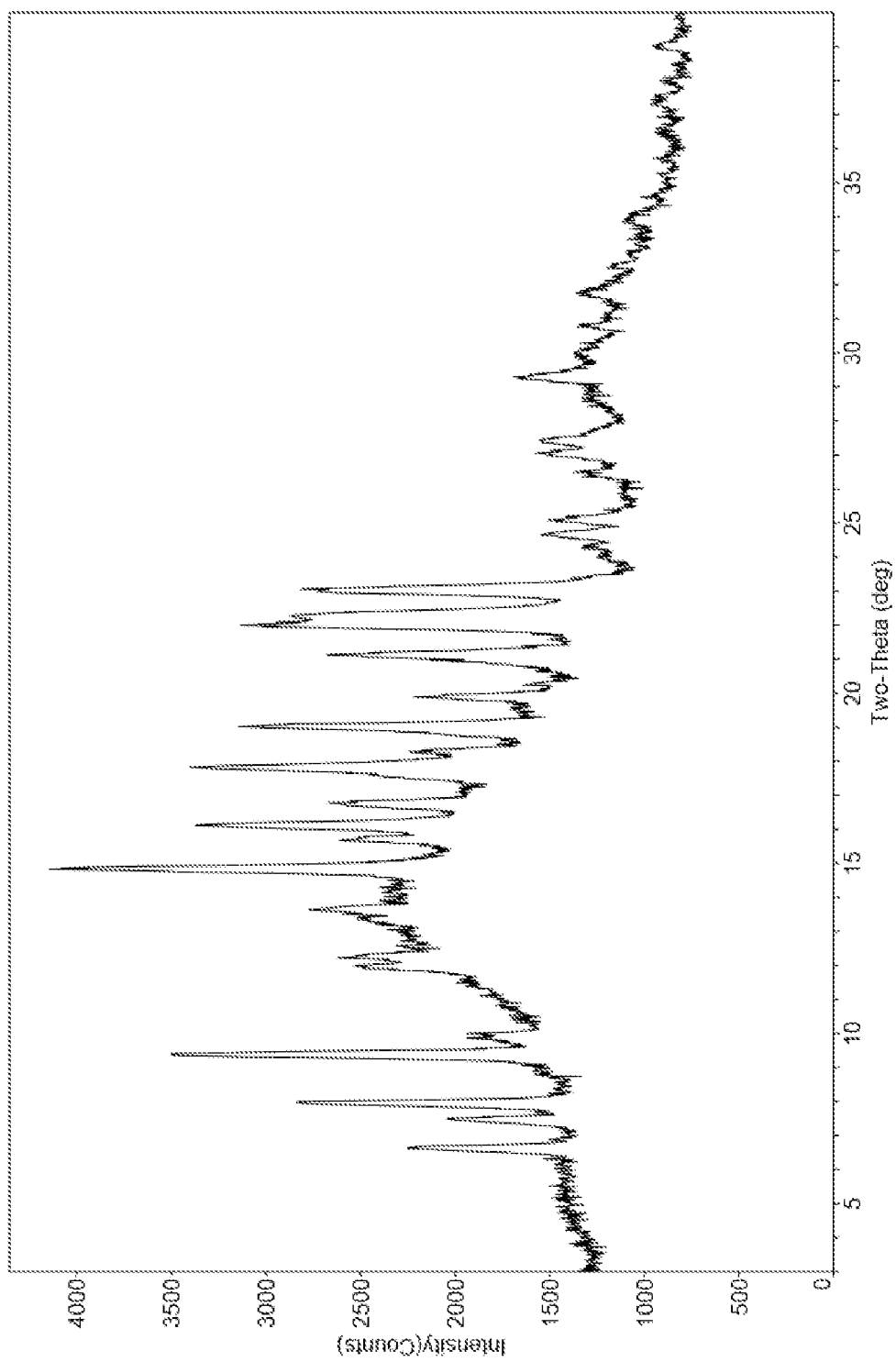
FIG. 5 depicts the XRPD spectrum of donepezil pamoate (1:1 ratio of donepezil to pamoic acid) obtained from donepezil hydrochloride and disodium pamoate in ethanol.

The XRPD pattern of an Example 5 salt is shown in FIG. 5. It is different from the XRPD patterns shown in FIG. 2 and FIG. 3. The interplanar spacing and intensity represents the typical relative intensities as set forth in Table 3. It was found that the solids obtained from this process converted to solids with the same XRPD pattern in FIG. 3 following reformation of a slurry in water. The key peaks are bolded and underlined in Table 3.

TABLE 3

| 2-Theta | d(A) | I % |
|---|---|---|
| 6.625 | 13.3308 | 43 |
| 7.497 | 11.7824 | 32.5 |
| 7.993 | 11.0526 | 70.7 |
| 9.371 | 9.43 | 100 |
| 9.993 | 8.844 | 17.1 |
| 11.981 | 7.3807 | 24.6 |
| 12.231 | 7.2306 | 25.5 |
| 13.338 | 6.6326 | 11 |
| 13.64 | 6.4864 | 26 |
| 14.826 | 5.9703 | 99.1 |
| 15.683 | 5.646 | 27.5 |
| 16.121 | 5.4934 | 68.8 |
| 16.767 | 5.2831 | 33.5 |
| 17.818 | 4.9739 | 79.9 |
| 18.274 | 4.8509 | 22.5 |
| 19.019 | 4.6623 | 76.3 |
| 19.895 | 4.459 | 35.5 |
| 21.118 | 4.2035 | 63.3 |
| 21.994 | 4.0379 | 85.9 |
| 22.261 | 3.9902 | 71.6 |
| 23.061 | 3.8535 | 74.4 |
| 23.994 | 3.7057 | 5.9 |
| 24.261 | 3.6656 | 9.2 |
| 24.664 | 3.6066 | 23.1 |
| 25.083 | 3.5473 | 16.3 |
| 26.497 | 3.3611 | 10.9 |
| 27.048 | 3.2939 | 23.5 |
| 27.447 | 3.2469 | 20.2 |
| 29.296 | 3.046 | 24 |
| 29.987 | 2.9774 | 6.8 |
| 30.769 | 2.9035 | 9.7 |
| 31.759 | 2.8152 | 12.5 |
| 32.537 | 2.7497 | 5.3 |
| 33.855 | 2.6455 | 7.9 |
| 35.721 | 2.5115 | 5.6 |
| 36.587 | 2.454 | 4.8 |
| 37.309 | 2.4082 | 6.3 |
| 37.996 | 2.3662 | 5.7 |
| 39.024 | 2.3062 | 8.8 |

Example 6: Characterization of Donepezil
Pamoates by Differential Scanning Calorimetry
(DSC), Thermogravimetric Analysis (TGA) and
Nuclear Magnetic Resonance Spectroscopy (NMR)

Figure 6:
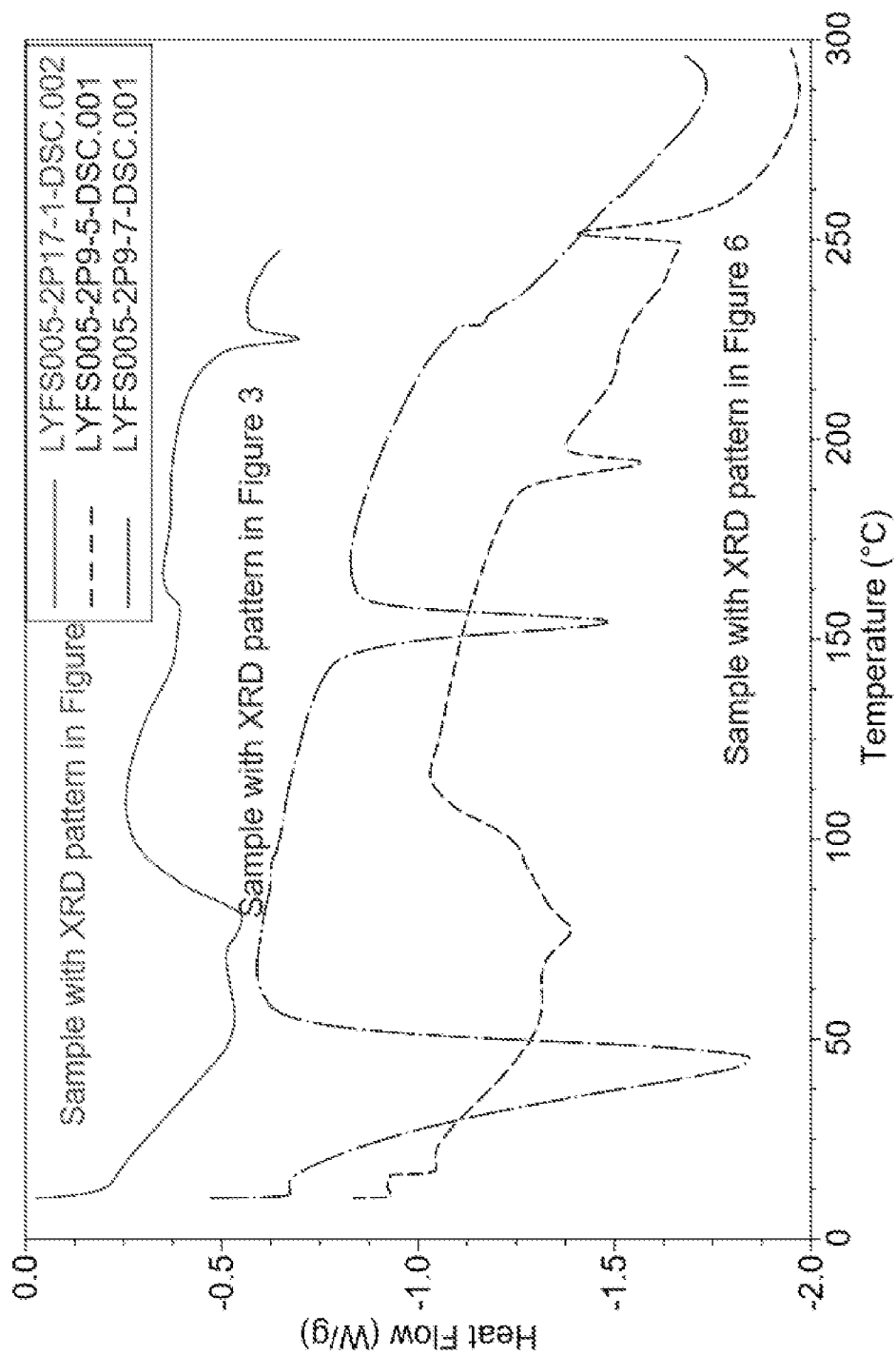
FIG. 6 depicts the differential scanning calorimetry thermograms of donepezil pamoate (1:1 and 2:1).
Figure 7:
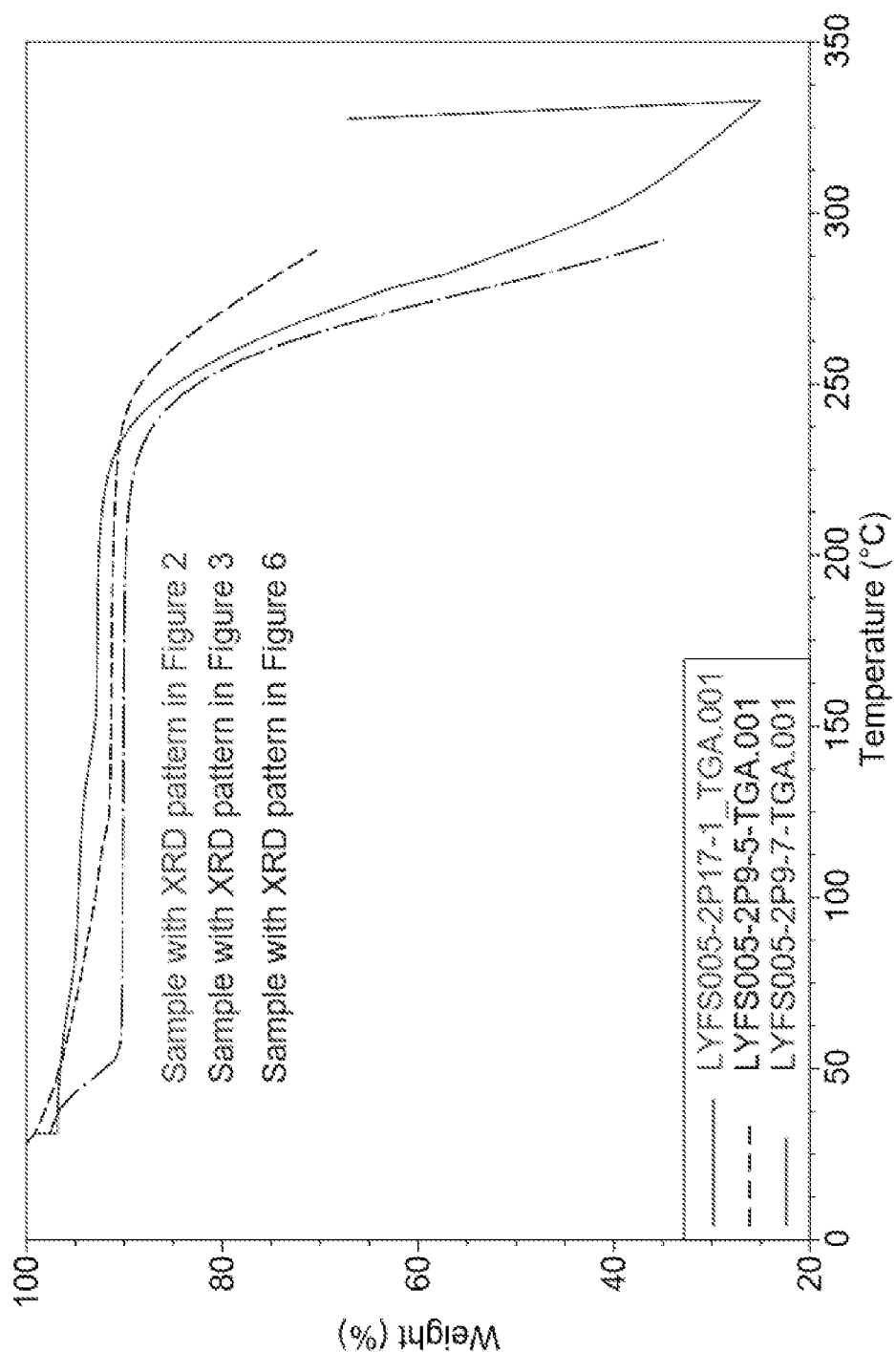
FIG. 7 depicts the thermogravimetric analysis thermograms of donepezil pamoate (1:1 and 2:1).

Donepezil pamoates (1:1 and 2:1) were analyzed using DSC, TGA and NMR. The DSC and TGA thermograms are shown in FIG. 6 and FIG. 7, respectively, indicating the existence of hydrates or solvates and presence of different crystal forms (polymorphic Form A and Form B).

Figure 8:
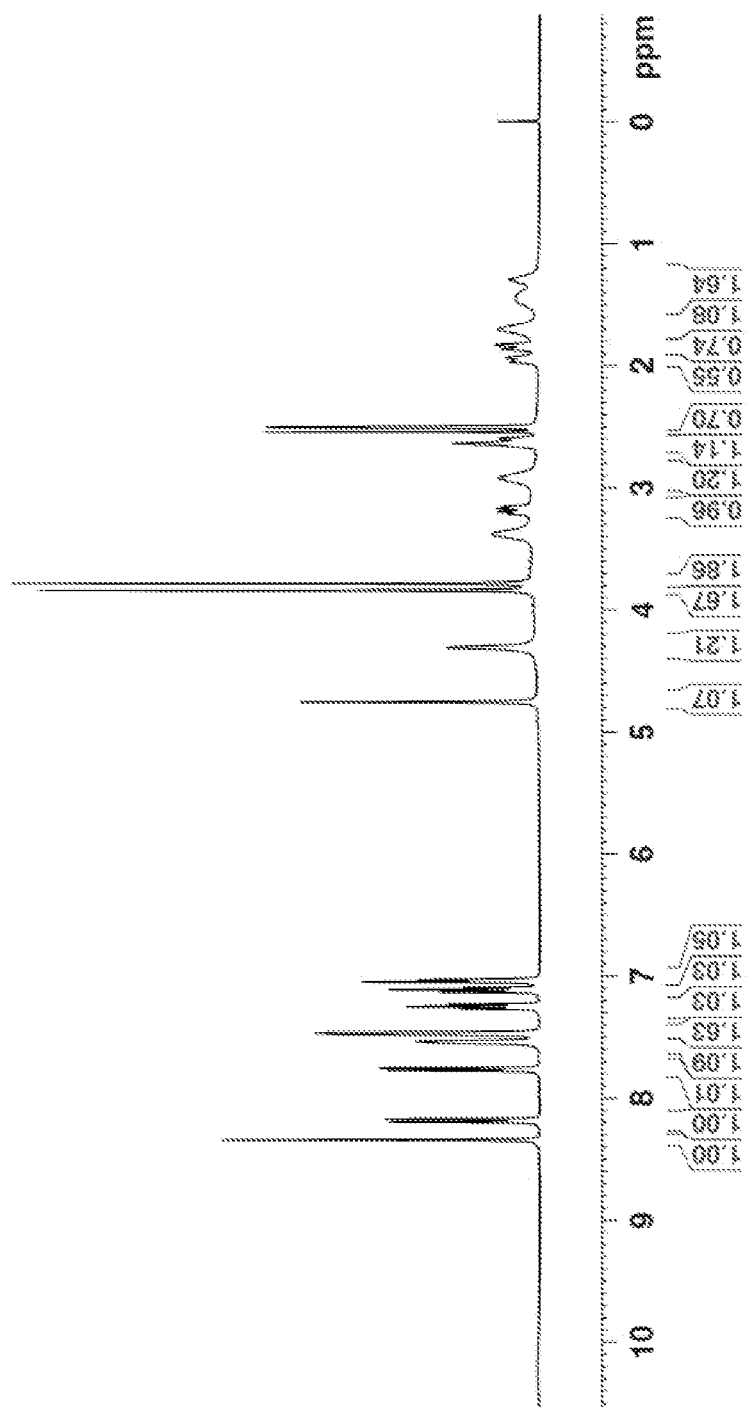
FIG. 8 depicts the NMR spectrum of donepezil pamoate (1:1 ratio of donepezil to pamoic acid) prepared in DMSO/water.
Figure 9:
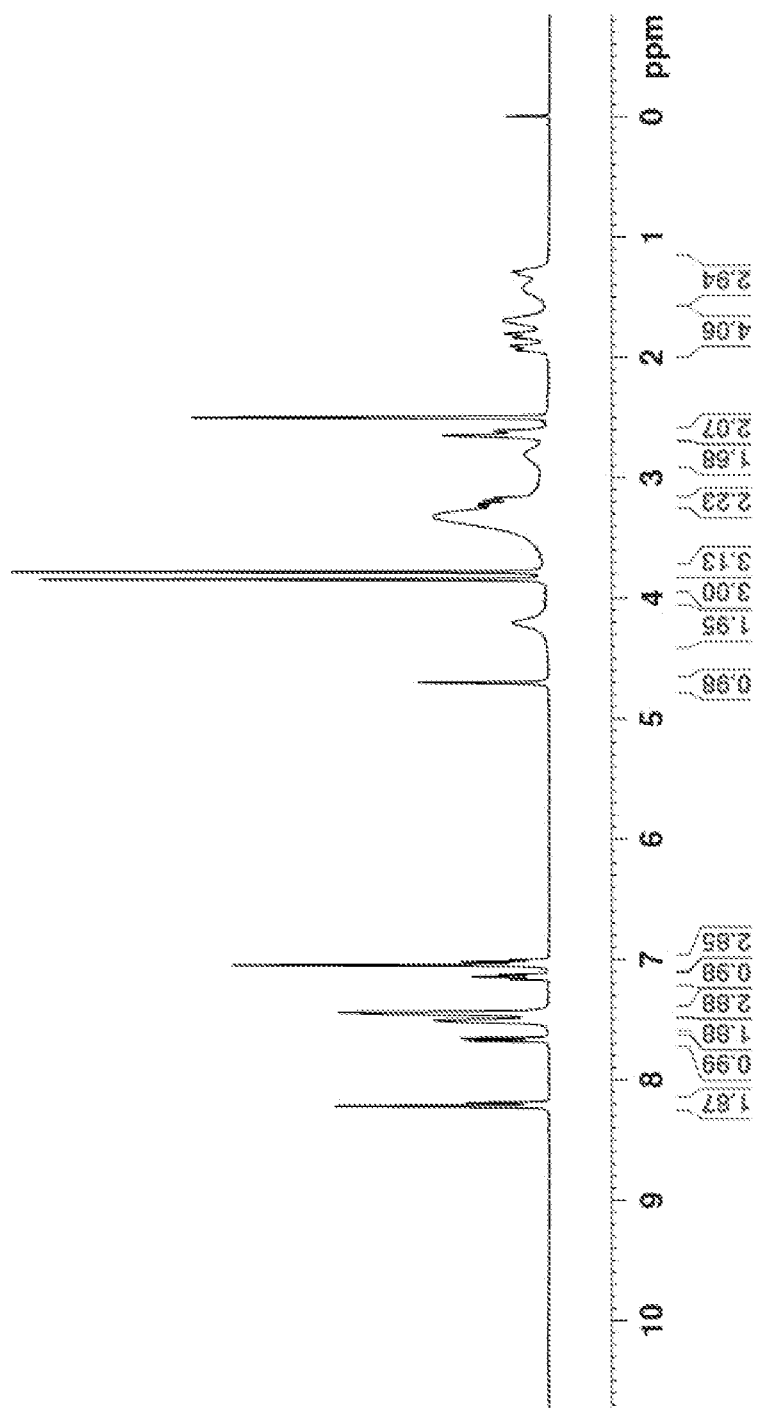
FIG. 9 depicts the NMR spectrum of donepezil pamoate (2:1 ratio of donepezil to pamoic acid) prepared in DMSO/water.
Figure 10:
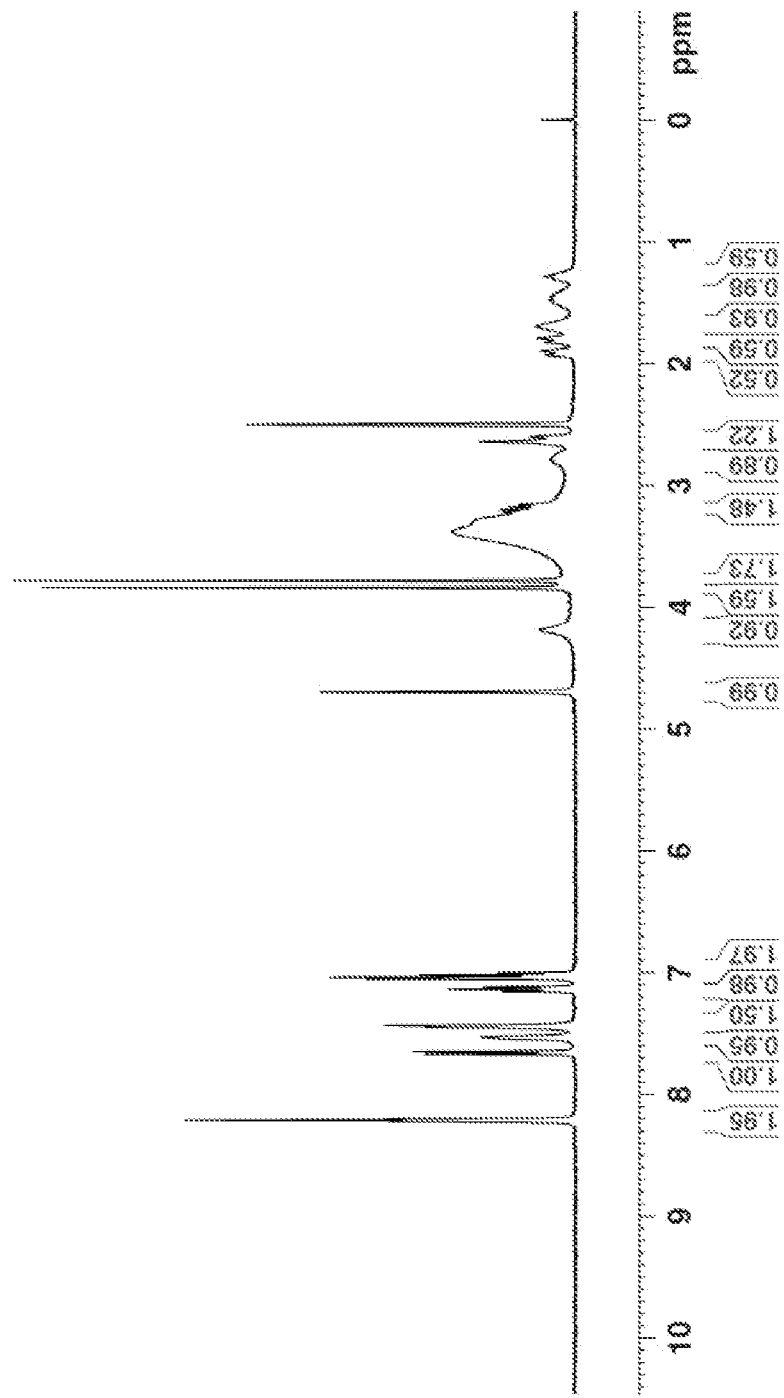
FIG. 10 depicts the NMR spectrum of donepezil pamoate (1:1 ratio of donepezil to pamoic acid) prepared in ethanol.

The NMR spectra are provided in FIGS. 8-10. FIG. 8 is the NMR spectrum of the 1:1 salt prepared in DMSO/water (XRPD Pattern with d spacing as shown in Table 1). The molar ratio of donepezil to pamoate was approximately 1:1 measured from proton integration of the $^1$H NMR spectrum. $^1$H NMR (400 MHz, DMSO-d6) chemical shifts were recorded at (all values in ppm) 8.34 (s, 2H), 8.18 (d, 2H), 7.76 (d, 2H), 7.53 (m, 2H), 7.47 (m, 3H), 7.25 (t, 2H), 7.11 (t, 3H), 7.04 (s, 2H), 4.76 (s, 2H), 4.31 (s, 2H), 3.84 (s, 3H), 3.79 (s, 3H), 3.18 (m, 1H), 2.92 (m, 2H), 2.62 (m, 2H), 1.97-1.30 (m, 9H). FIG. 9 is the NMR spectrum of the 2:1 salt prepared in DMSO/water (XRPD Pattern with d spacing as shown in Table 2). The molar ratio of donepezil to pamoate was approximately 2:1 measured from proton integration of the $^1$H NMR spectrum. $^1$H NMR (400 MHz, DMSO-d6) chemical shifts were recorded at (in ppm) 8.21 (m, 4H), 7.67 (d, 2H), 7.75-7.44 (m, 10H), 7.15 (t, 2H), 7.02 (m, 6H), 4.71 (s, 2H), 4.21 (s, 4H), 3.85 (s, 6H), 3.78 (s, 6H), 3.21 (m, 2H), 2.81 (m, 4H), 2.61 (m, 4H), 1.94-1.30 (m, 18H). FIG. 10 is the NMR spectrum of the 1:1 salt prepared in ethanol (XRPD Pattern with d spacing as shown in Table 3). The molar ratio of donepezil to pamoate was approximately 1:1 measured from proton integration of the $^1$H NMR spectrum. $^1$H NMR (400 MHz, DMSO-d6) chemical shifts were recorded at (in ppm) 8.21 (m, 4H), 7.65 (d, 2H), 7.44 (m, 2H), 7.43 (m, 3H), 7.14 (t, 2H), 7.03 (m, 4H), 4.70 (s, 2H), 4.19 (s, 2H), 3.84 (s, 3H), 3.78 (s, 3H), 3.21 (m, 1H), 2.78 (m, 2H), 2.62 (m, 2H), 1.93-1.27 (m, 9H).

Example 7: A Comparison of In Vivo Absorption
of Donepezil Pamoate in Rats Following a Single
Intramuscular Dose with Donepezil Pamoate (2:1)

Physicochemical characterization studies have showed that donepezil pamoate (2:1) is the most stable form of donepezil pamoate salt. Therefore, a pharmacokinetic study was performed in rat model to evaluate in vivo absorption characteristics of the donepezil pamoate (2:1) following a single dose intramuscular administration using donepezil hydrochloride solution as a reference. Ten (10) female rats that weighed 300±30 grams were randomly divided into 2 groups of 5 rats each. Donepezil pamoate (2:1) suspension and donepezil hydrochloride solution were administered to each group, respectively, through intramuscular (IM) injection into the rear legs at a dose of 13.5 mg/kg (in donepezil). In the pharmacokinetic study, donepezil hydrochloride solution were prepared using saline solution, donepezil pamoate (2:1) is suspended using the diluent which is composed of carboxymethylcellulose sodium, mannitol, polysorbate 80, sodium hydroxide and/or hydrochloric acid for pH adjustment, and water for injection. Blood samples were collected and transferred into tubes containing anticoagulant, heparin. The plasma samples were separated into labeled tubes and stored frozen at −20° C. until they were analyzed using a HPLC-MS method. 500 µL of blood was drawn for each time point. The time intervals selected to obtain plasma samples were 15 minutes, 30 minutes, 45 minutes, 60 minutes, 90 minutes, 2 hours, 4 hours, 6 hours, 8 hours, 12 hours, 24 hours and 48 hours, for the donepezil hydrochloride solution injection and 30 minutes, 90 minutes, 2 hours, 4 hours, 8 hours, 24 hours, 48 hours, 56 hours, 72 hours, 144 hours, 192 hours, 288 hours and 336 hours for the Donepezil pamoate (2:1) suspension injection, respectively.

Figure 11:
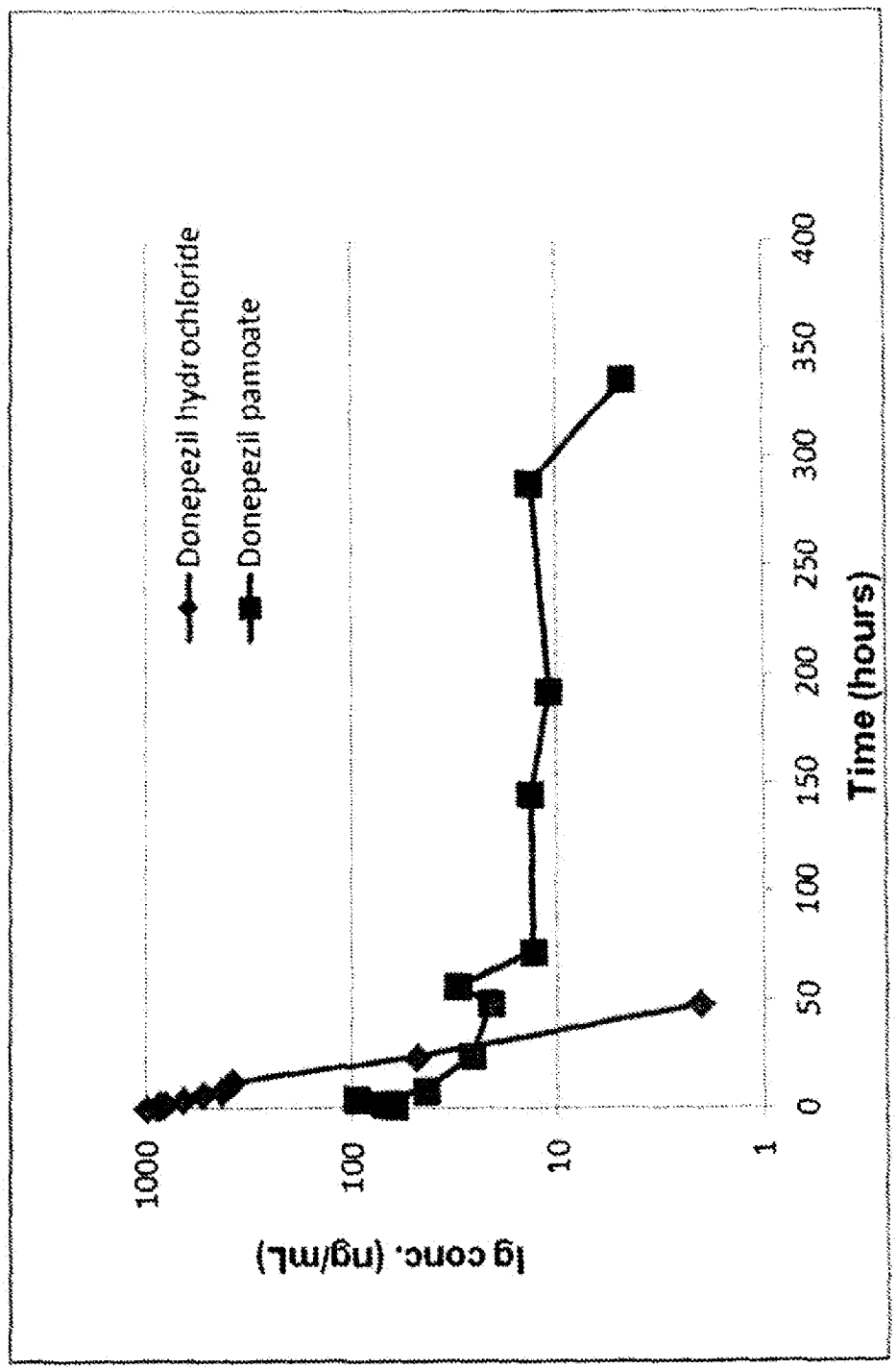
FIG. 11 depicts the mean plasma concentration of donepezil after a single dose (13.5 mg/kg) of an intramuscular injection of donepezil pamoate (2:1) suspension (n=5) and donepezil hydrochloride solution (n=5) in female rats respectively as shown in Example 7.

The results are shown in FIG. 11. Specifically, FIG. 11 demonstrates that donepezil hydrochloride salt solution is rapidly absorbed and then eliminated after a single intramuscular injection. In contrast, after a single intramuscular injection of the donepezil pamoate (2.1), a sustained level of donepezil plasma concentrations was maintained following an initial faster absorption within the first hour thereby demonstrating that extended release of donepezil was achieved using donepezil pamoate.

Example 8: Summary of Donepezil Pamoate Salt
Screen with Different Solvent Systems This example provides a summary of the donepezil pamoate salt screens described in the above examples. The inventors found that the solvent to prepare the salt was important as many salts did not work for salt formation.

When ethanol (the amount of ethanol that can be used is enough to dissolve the donepezil free base; in fact, the ratio of free base to ethanol can be as high as 5:1 free base to ethanol) and pamoic acid (the acid to ethanol ratio can be as high as 10:1 pamoic acid to ethanol), are used as solvent system for salt formation, a mono-pamoate salt of donepezil is obtained exclusively regardless of the ratio of the free base of donepezil and pamoic acid used.

When DMSO and water is used as solvent system for salt formation, a mono-pamoate salt is obtained if a 1:1 ratio of the free base of donepezil and pamoic acid is used and a semi-pamoate salt of the product is obtained if a 2:1 ratio of the free base of donepezil and pamoic acid is used.

When water (the ratio of free base to water that can be used is 70:1 and the ratio of the acid to water is about 180:1) is used as solvent system for salt formation, a semi-pamoate salt of donepezil is the only product obtained when a 1:1 or 2:1 ratio of the free base of donepezil and pamoic acid is used.

Table 4 below describes the various solvents that can be used to obtain pamoate salts of donepezil.

TABLE 4

| Solvent | Ratio of free base of donepezil to pamoic acid | Salt obtained |
|---|---|---|
| Ethanol | 1:1 and 2:1 | Mono-pamoate is obtained only |
| DMSO and water | 1:1 | Mono-pamoate of donepezil |
| DMSO and water | 2:1 | Semi-pamoate of donepezil |
| Water alone | 1:1 or 2:1 | Semi-pamoate salt of donepezil is obtained only |

All pamoate salts obtained using the above solvent systems contain about 4-9% (by weight) of water content based on loss on dry studies. The donepezil pamoate salt (hydrated, 2:1 ratio) is the most stable salt. When this hydrated salt is heated at an elevated temperature (such as up to 120° C.) it will convert to the anhydrous form which is not stable. At this point, the anhydrous form will absorb moisture from the atmosphere and gradually convert back to the hydrate form.

Example 9: Polymorph Studies 2080 mg of donepezil HCl is weighed and dissolved in 30 mL of water while stirring to provide Solution A. 1075 mg of pamoate disodium is weighed and dissolved in 6 mL of water while stirring to provide Solution B. Solution A is added into Solution B to which 40 mL of water was added. The resulting solution was stirred for at least 3 hours before being filtered. The solid material obtained from filtration is dried under vacuum to yield Donepezil pamoate salt. The X-ray powder diffraction, thermogravimetric analysis/differential scanning calorimetry and H-studies of this salt identified this salt as "Hydrated Form". The hydrated salt can be converted into another polymorphic form (designated as "Anhydrous Form") when dried at 120° C. The X-ray powder diffraction data for Hydrated (Also referred to as "Form A" herein) and Anhydrous Forms (Also referred to as "Form B" herein) are shown in FIGS. 12 and 13. The Hydrated Form is characterized with X-ray powder diffraction as shown in FIG. 12. The X-ray powder diffraction data is also shown below in Table 5. The key peaks are bolded and underlined in Table 5.

TABLE 5

| 2-Theta | d | Height | I % | Area | I % |
|---|---|---|---|---|---|
| 6.183 | 14.2818 | 605 | 16.9 | 9294 | 15.6 |
| 8.606 | 10.266 | 682 | 19.1 | 8941 | 15 |
| 9.446 | 9.3545 | 197 | 5.5 | 3498 | 5.9 |
| 9.706 | 9.1052 | 223 | 6.2 | 3479 | 5.8 |
| 10.425 | 8.4786 | 207 | 5.8 | 2887 | 4.9 |
| 11.592 | 7.6278 | 3574 | 100 | 50863 | 85.5 |
| 12.271 | 7.2072 | 2337 | 65.4 | 34990 | 58.8 |
| 13.354 | 6.625 | 797 | 22.3 | 15340 | 25.8 |
| 13.812 | 6.4059 | 1112 | 31.1 | 19587 | 32.9 |
| 15.274 | 5.7961 | 1110 | 31.1 | 12662 | 21.3 |
| 15.814 | 5.5992 | 810 | 22.7 | 11667 | 19.6 |
| 16.296 | 5.4348 | 1198 | 33.5 | 15006 | 25.2 |
| 16.936 | 5.2308 | 971 | 27.2 | 19618 | 33 |
| 17.216 | 5.1464 | 578 | 16.2 | 12703 | 21.3 |
| 17.978 | 4.9301 | 694 | 19.4 | 9583 | 16.1 |
| 18.84 | 4.7063 | 1053 | 29.5 | 34003 | 57.1 |
| 19.259 | 4.6049 | 2644 | 74 | 43674 | 73.4 |
| 20.041 | 4.4269 | 1512 | 42.3 | 30683 | 51.6 |
| 21.301 | 4.1677 | 2375 | 66.5 | 44297 | 74.4 |
| 21.802 | 4.0732 | 647 | 18.1 | 13745 | 23.1 |
| 22.503 | 3.9478 | 504 | 14.1 | 8412 | 14.1 |
| 23.304 | 3.8138 | 2350 | 65.8 | 43783 | 73.6 |
| 23.583 | 3.7694 | 1098 | 30.7 | 34544 | 58 |
| 24.246 | 3.6678 | 612 | 17.1 | 16323 | 27.4 |
| 24.644 | 3.6094 | 1403 | 39.3 | 34239 | 57.5 |
| 25.308 | 3.5162 | 292 | 8.2 | 5300 | 8.9 |
| 26.426 | 3.3699 | 261 | 7.3 | 2243 | 3.8 |
| 27.31 | 3.2628 | 1058 | 29.6 | 50410 | 84.7 |
| 27.67 | 3.2213 | 2016 | 56.4 | 59519 | 100 |
| 29.152 | 3.0607 | 193 | 5.4 | 5352 | 9 |
| 29.772 | 2.9984 | 173 | 4.8 | 3892 | 6.5 |
| 30.675 | 2.9122 | 176 | 4.9 | 3910 | 6.6 |
| 31.133 | 2.8704 | 237 | 6.6 | 4714 | 7.9 |
| 31.955 | 2.7984 | 204 | 5.7 | 5324 | 8.9 |
| 32.378 | 2.7628 | 133 | 3.7 | 4691 | 7.9 |
| 32.949 | 2.7162 | 84 | 2.4 | 566 | 1 |
| 33.458 | 2.676 | 216 | 6 | 3508 | 5.9 |
| 34.601 | 2.5902 | 171 | 4.8 | 3235 | 5.4 |
| 36.138 | 2.4835 | 296 | 8.3 | 6286 | 10.6 |
| 37.426 | 2.4009 | 101 | 2.8 | 860 | 1.4 |
| 38.329 | 2.3464 | 98 | 2.7 | 1792 | 3 |

The Anhydrous Form is characterized with X-ray powder diffraction as shown in FIG. 13. The X-ray powder diffraction data is also shown below in Table 6. The key peaks are bolded and underlined in Table 6.

TABLE 6

| 2-Theta | d | Height | I % | Area | I % |
|---|---|---|---|---|---|
| 6.309 | 13.9981 | 398 | 35.3 | 4702 | 25.4 |
| 8.484 | 10.4131 | 264 | 23.4 | 3600 | 19.5 |
| 9.23 | 9.5737 | 246 | 21.8 | 2083 | 11.3 |
| 9.851 | 8.9711 | 138 | 12.3 | 2478 | 13.4 |

TABLE 6-continued

| 2-Theta | d | Height | I % | Area | I % |
|---|---|---|---|---|---|
| 10.386 | 8.51 | 215 | 19.1 | 3508 | 19 |
| 11.912 | 7.4232 | 1126 | 100 | 18504 | 100 |
| 12.724 | 6.9512 | 112 | 9.9 | 891 | 4.8 |
| 13.97 | 6.3342 | 328 | 29.1 | 5955 | 32.2 |
| 14.211 | 6.227 | 209 | 18.6 | 6470 | 35 |
| 14.833 | 5.9675 | 201 | 17.9 | 1980 | 10.7 |
| 15.452 | 5.7297 | 175 | 15.5 | 1302 | 7 |
| 16.157 | 5.4814 | 356 | 31.6 | 5170 | 27.9 |
| 16.811 | 5.2695 | 138 | 12.3 | 621 | 3.4 |
| 17.196 | 5.1523 | 169 | 15 | 3960 | 21.4 |
| 17.638 | 5.0242 | 158 | 14 | 3390 | 18.3 |
| 18.225 | 4.8637 | 88 | 7.8 | 1884 | 10.2 |
| 18.479 | 4.7975 | 96 | 8.5 | 1878 | 10.1 |
| 19.716 | 4.499 | 373 | 33.1 | 4130 | 22.3 |
| 20.362 | 4.3577 | 364 | 32.3 | 6536 | 35.3 |
| 21.082 | 4.2107 | 403 | 35.8 | 5197 | 28.1 |
| 22.226 | 3.9964 | 123 | 10.9 | 2750 | 14.9 |
| 22.583 | 3.9339 | 126 | 11.2 | 2755 | 14.9 |
| 23.704 | 3.7504 | 431 | 38.3 | 7905 | 42.7 |
| 24.185 | 3.677 | 211 | 18.7 | 5368 | 29 |
| 24.907 | 3.572 | 157 | 13.9 | 1194 | 6.5 |
| 25.93 | 3.4333 | 86 | 7.6 | 1507 | 8.1 |
| 27.99 | 3.1851 | 125 | 11.1 | 3291 | 17.8 |
| 28.593 | 3.1194 | 108 | 9.6 | 756 | 4.1 |

Example 10: Preparation of Rivastigmine Pamoate Salt

Figure 14:
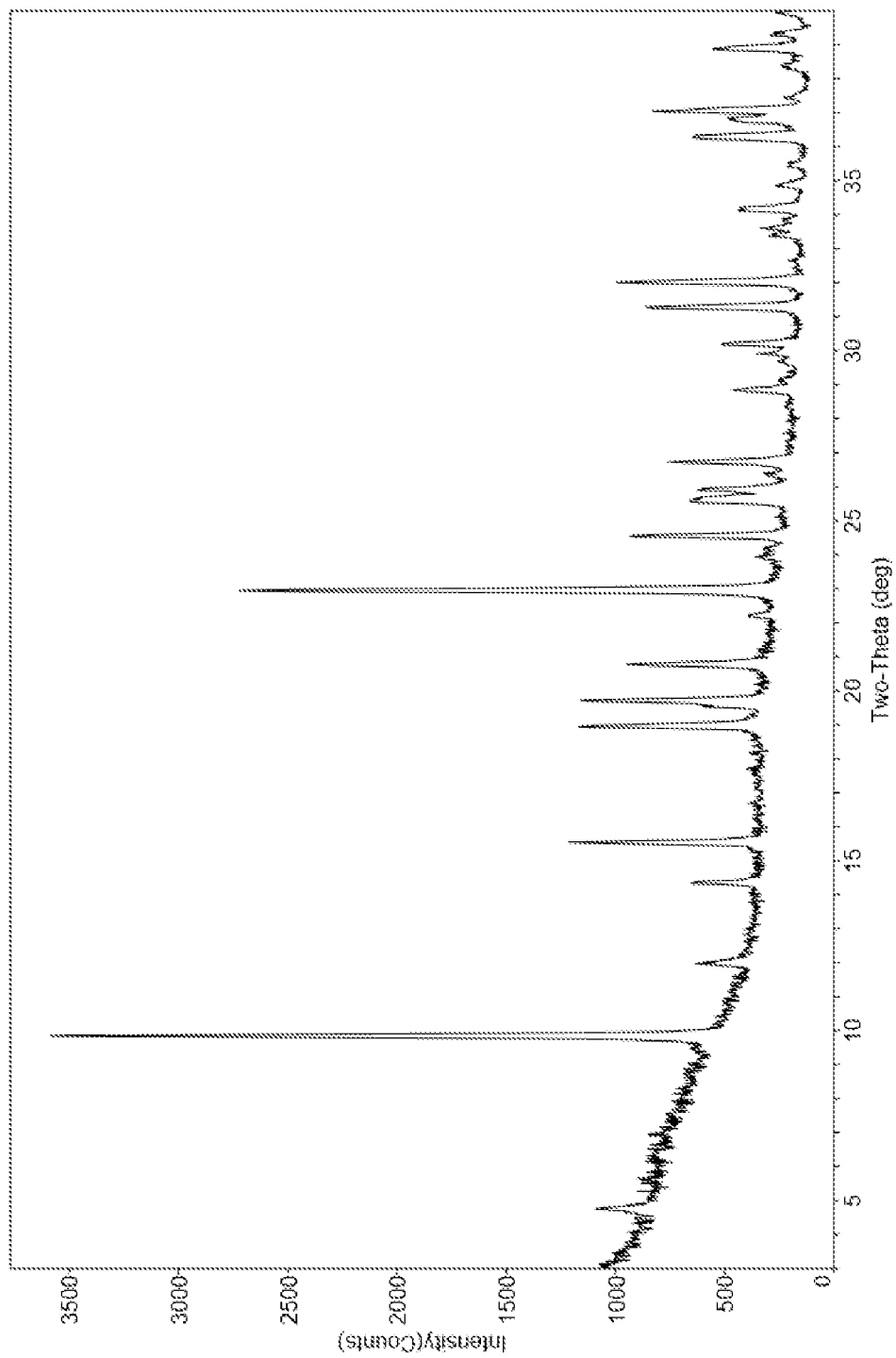
FIG. 14 depicts an X-ray powder diffraction spectrum of rivastigmine pamoate salt as described in Example 10.
Figure 15:
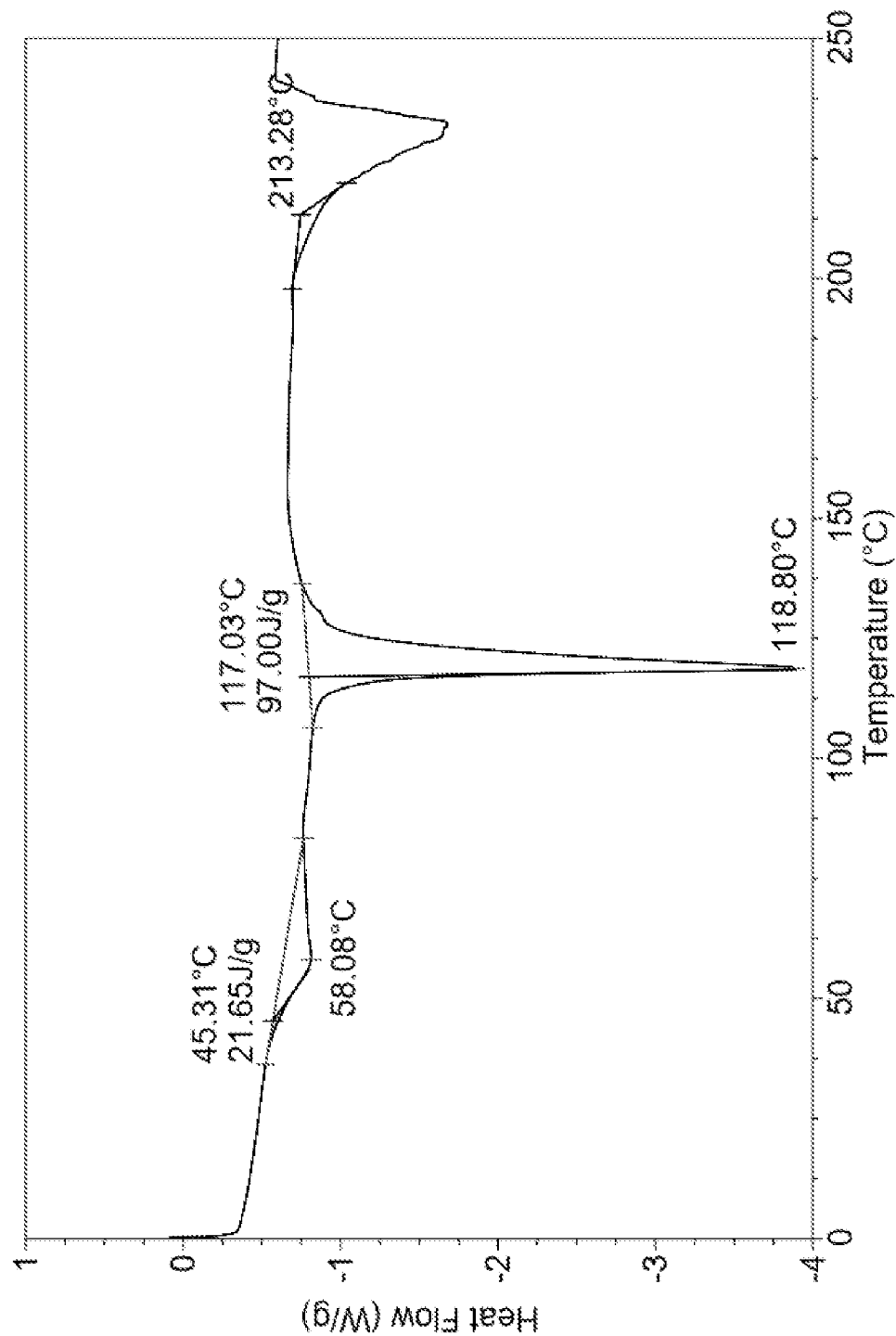
FIG. 15 depicts the differential calorimetry diagram for rivastigimine pamoate salt as described in Example 10.
Figure 16:
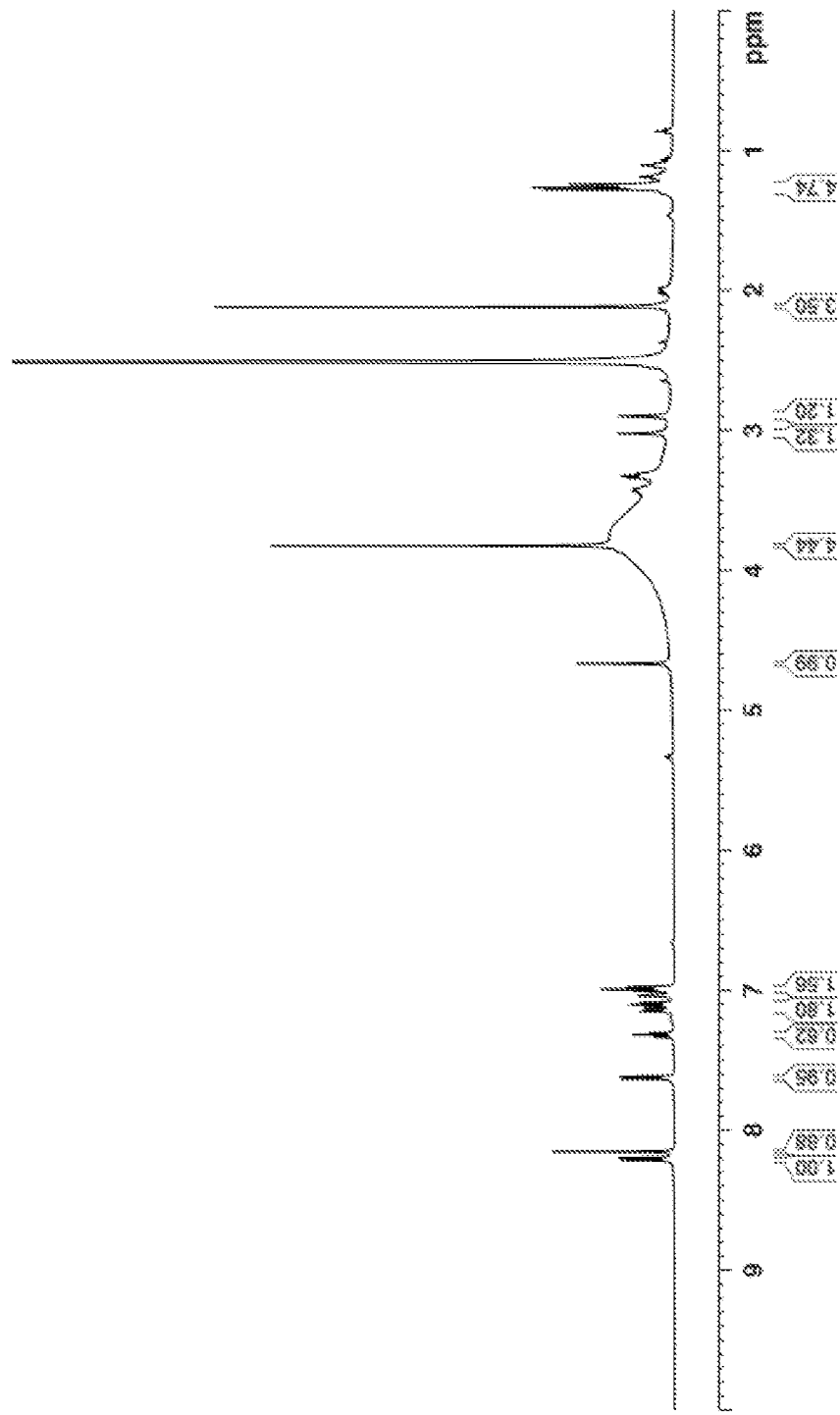
FIG. 16 depicts the NMR spectra of rivastigmine pamoate salt as described in Example 10.

A solution of 20 mg of rivastigmine tartrate in 0.25 mL ethanol was added to a solution of 20 mg of pamoate disodium salt in 0.25 mL ethanol. The resulting solution was stirred for 4 hours and then centrifuged. The wet product was dried at 60° C. under vacuum to yield a Rivastigamine pamoate salt (1:1 ratio). The salt is characterized with X-ray powder diffraction, differential scanning calorimetry and NMR as shown in FIGS. 14-16. The X-ray powder diffraction data is also shown below in Table 7. The key peaks are bolded and underlined in Table 7.

TABLE 7

| 2-Theta | d | Height | I % | Area | I % |
|---|---|---|---|---|---|
| 4.756 | 18.5639 | 239 | 7.8 | 2036 | 9.1 |
| 9.847 | 8.9754 | 3046 | 100 | 22438 | 100 |
| 11.965 | 7.3906 | 220 | 7.2 | 1489 | 6.6 |
| 14.334 | 6.1738 | 302 | 9.9 | 2384 | 10.6 |
| 15.546 | 5.6952 | 873 | 28.7 | 6489 | 28.9 |
| 18.946 | 4.6803 | 828 | 27.2 | 7948 | 35.4 |
| 19.707 | 4.5011 | 821 | 27 | 7558 | 33.7 |
| 20.773 | 4.2724 | 637 | 20.9 | 5831 | 26 |
| 22.221 | 3.9972 | 103 | 3.4 | 1046 | 4.7 |
| 22.947 | 3.8724 | 2461 | 80.8 | 21213 | 94.5 |
| 23.939 | 3.7142 | 118 | 3.9 | 1898 | 8.5 |
| 24.168 | 3.6795 | 82 | 2.7 | 2194 | 9.8 |
| 24.55 | 3.6231 | 705 | 23.1 | 6215 | 27.7 |
| 25.563 | 3.4818 | 428 | 14.1 | 6626 | 29.5 |
| 25.907 | 3.4363 | 383 | 12.6 | 4060 | 18.1 |
| 26.396 | 3.3738 | 81 | 2.7 | 658 | 2.9 |
| 26.725 | 3.3329 | 536 | 17.6 | 4835 | 21.5 |
| 28.841 | 3.093 | 283 | 9.3 | 3277 | 14.6 |
| 29.697 | 3.0058 | 77 | 2.5 | 958 | 4.3 |
| 29.91 | 2.9849 | 177 | 5.8 | 2675 | 11.9 |
| 30.179 | 2.9589 | 345 | 11.3 | 3663 | 16.3 |
| 31.28 | 2.8572 | 697 | 22.9 | 5959 | 26.6 |
| 32.007 | 2.7939 | 840 | 27.6 | 7422 | 33.1 |
| 33.384 | 2.6818 | 132 | 4.3 | 1242 | 5.5 |
| 33.607 | 2.6645 | 186 | 6.1 | 3699 | 16.5 |
| 34.143 | 2.6239 | 285 | 9.4 | 4799 | 21.4 |
| 34.849 | 2.5723 | 115 | 3.8 | 963 | 4.3 |
| 35.426 | 2.5317 | 75 | 2.5 | 716 | 3.2 |
| 36.278 | 2.4742 | 503 | 16.5 | 6085 | 27.1 |

TABLE 7-continued

| 2-Theta | d | Height | I % | Area | I % |
|---|---|---|---|---|---|
| 36.847 | 2.4373 | 349 | 11.5 | 8055 | 35.9 |
| 37.042 | 2.4249 | 699 | 22.9 | 8699 | 38.8 |
| 37.442 | 2.3999 | 70 | 2.3 | 292 | 1.3 |
| 38.396 | 2.3425 | 90 | 3 | 870 | 3.9 |
| 38.889 | 2.3139 | 427 | 14 | 6105 | 27.2 |
| 39.279 | 2.2918 | 155 | 5.1 | 1435 | 6.4 |
| 39.901 | 2.2575 | 23 | 0.8 | −230 | −1 |

Example 11: Preparation of Memantine Pamoate Salt

Figure 17:
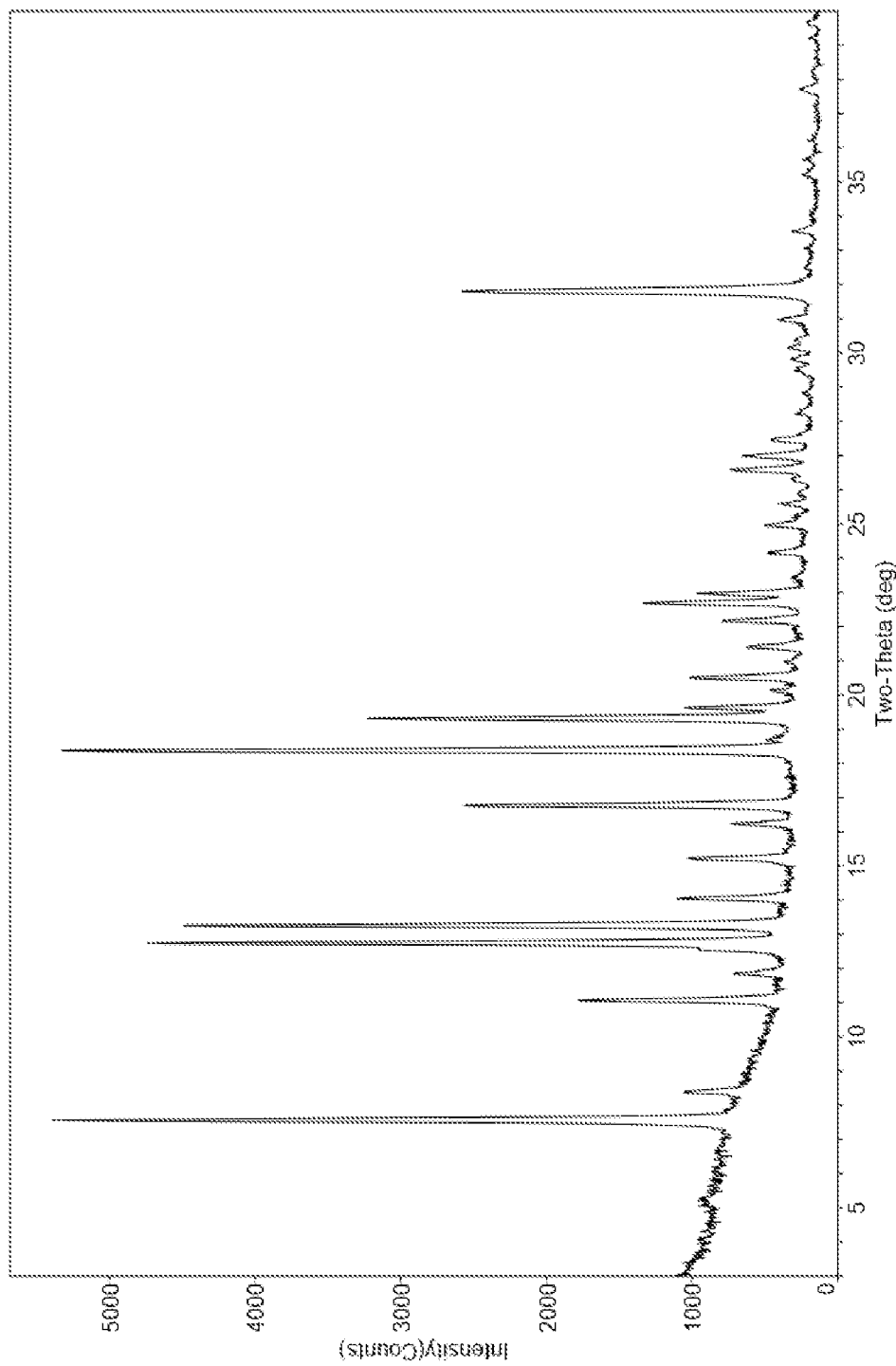
FIG. 17 depicts an X-ray powder diffraction spectrum of memantine pamoate salt as described in Example 11.
Figure 18:
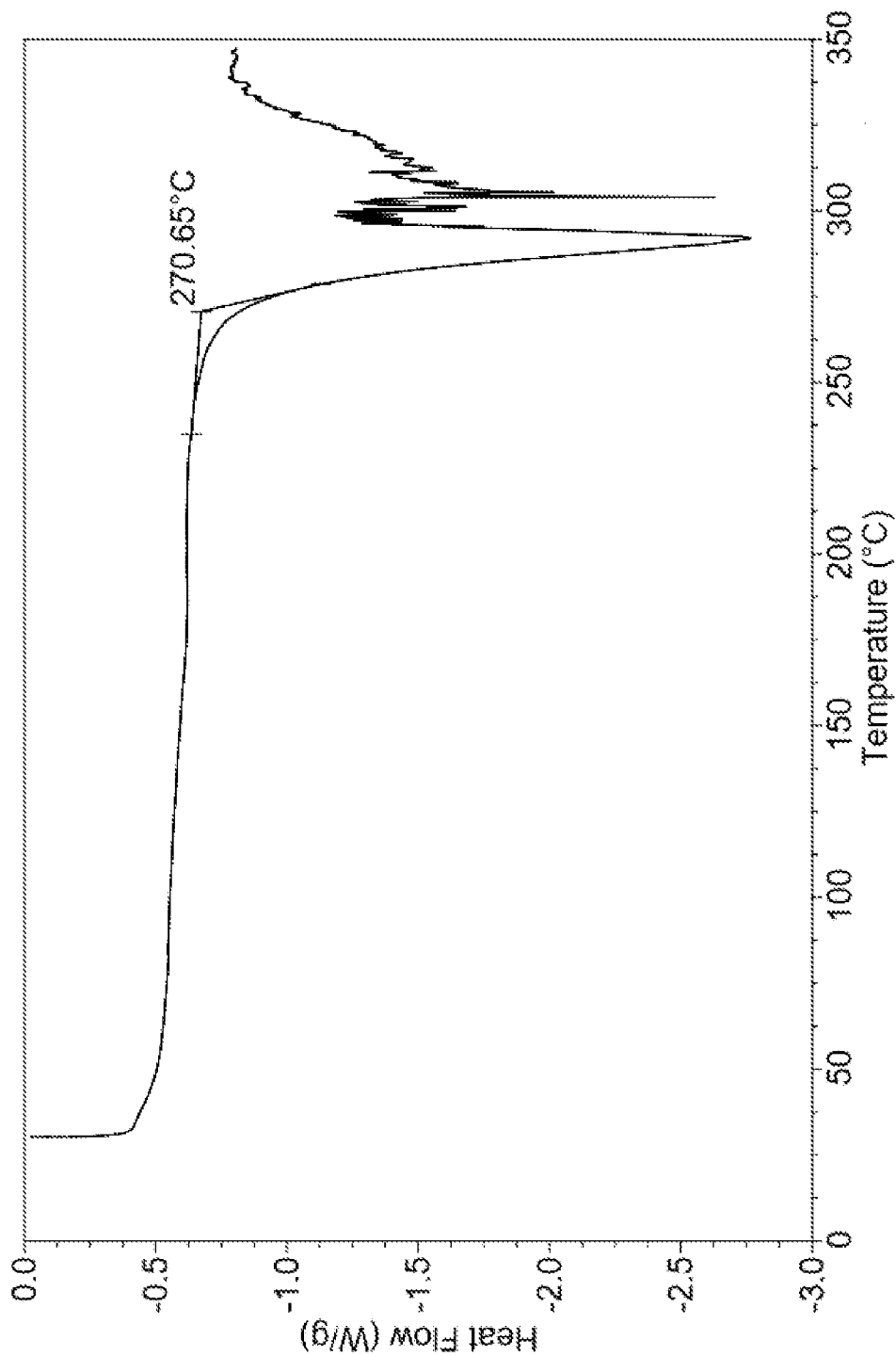
FIG. 18 depicts the differential calorimetry diagram for memantine pamoate salt as described in Example 11.
Figure 19:
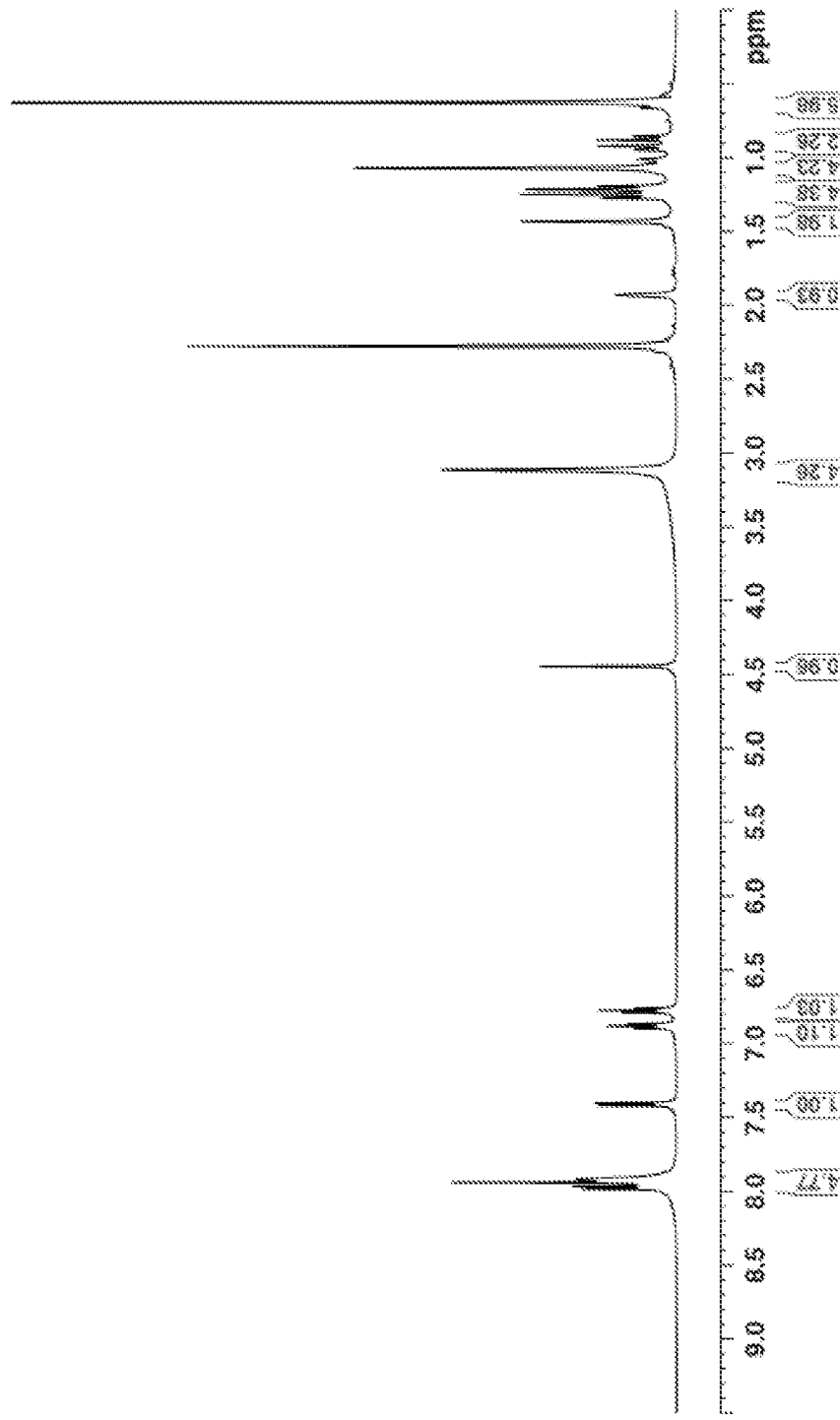
FIG. 19 depicts the NMR spectra of memantine pamoate salt as described in Example 11.

A solution of 22 mg of memantine hydrochloride in 0.25 mL ethanol was added to a solution of 39 mg of pamoate disodium salt in 0.25 mL ethanol. The resulting solution was stirred at room temperature for 4 hours and then centrifuged. The wet product obtained was dried at 60° C. under the vacuum to yield memantine pamoate salt (1:1 ratio). The salt is characterized with X-ray powder diffraction, differential scanning calorimetry and NMR as shown in FIGS. 17-19. The X-ray powder diffraction data is also shown below in Table 8. The key peaks are bolded and underlined in Table 8.

TABLE 8

| 2-Theta | d | Height | I % | Area | I % |
|---|---|---|---|---|---|
| 5.217 | 16.9248 | 117 | 2.3 | 1668 | 4.2 |
| 7.559 | 11.6862 | 4673 | 93.3 | 37155 | 92.6 |
| 8.381 | 10.5414 | 370 | 7.4 | 2170 | 5.4 |
| 11.066 | 7.9886 | 1360 | 27.2 | 9847 | 24.5 |
| 11.836 | 7.4705 | 310 | 6.2 | 2013 | 5 |
| 12.743 | 6.941 | 4358 | 87.1 | 36773 | 91.6 |
| 13.243 | 6.6801 | 4129 | 82.5 | 32226 | 80.3 |
| 14.043 | 6.3013 | 728 | 14.5 | 4119 | 10.3 |
| 15.222 | 5.8156 | 689 | 13.8 | 5442 | 13.6 |
| 16.232 | 5.4562 | 417 | 8.3 | 3323 | 8.3 |
| 16.768 | 5.2828 | 2267 | 45.3 | 19323 | 48.1 |
| 18.37 | 4.8256 | 5006 | 100 | 40141 | 100 |
| 19.306 | 4.5937 | 2896 | 57.9 | 23722 | 59.1 |
| 19.627 | 4.5194 | 720 | 14.4 | 5871 | 14.6 |
| 20.135 | 4.4064 | 161 | 3.2 | 1233 | 3.1 |
| 20.506 | 4.3275 | 708 | 14.1 | 5723 | 14.3 |
| 20.973 | 4.2321 | 81 | 1.6 | 195 | 0.5 |
| 21.388 | 4.1511 | 357 | 7.1 | 2768 | 6.9 |
| 22.151 | 4.0098 | 518 | 10.3 | 4298 | 10.7 |
| 22.681 | 3.9172 | 1087 | 21.7 | 9862 | 24.6 |
| 22.966 | 3.8693 | 701 | 14 | 6183 | 15.4 |
| 23.427 | 3.7942 | 57 | 1.1 | −227 | −0.6 |
| 24.138 | 3.684 | 249 | 5 | 1989 | 5 |
| 24.952 | 3.5656 | 279 | 5.6 | 2774 | 6.9 |
| 25.595 | 3.4774 | 190 | 3.8 | 1716 | 4.3 |
| 25.884 | 3.4393 | 61 | 1.2 | 600 | 1.5 |
| 26.305 | 3.3852 | 107 | 2.1 | 1193 | 3 |
| 26.588 | 3.3497 | 523 | 10.4 | 6016 | 15 |
| 26.99 | 3.3008 | 461 | 9.2 | 5102 | 12.7 |
| 27.45 | 3.2466 | 245 | 4.9 | 2441 | 6.1 |
| 28.219 | 3.1598 | 100 | 2 | 1313 | 3.3 |
| 28.834 | 3.0938 | 53 | 1.1 | 194 | 0.5 |
| 29.473 | 3.0281 | 108 | 2.2 | 1179 | 2.9 |
| 29.828 | 2.993 | 118 | 2.4 | 936 | 2.3 |
| 30.142 | 2.9624 | 140 | 2.8 | 2145 | 5.3 |
| 30.367 | 2.941 | 82 | 1.6 | 1452 | 3.6 |
| 30.976 | 2.8846 | 204 | 4.1 | 1994 | 5 |
| 31.797 | 2.8119 | 2387 | 47.7 | 26003 | 64.8 |
| 33.553 | 2.6686 | 162 | 3.2 | 1657 | 4.1 |
| 35.213 | 2.5466 | 98 | 2 | 1279 | 3.2 |
| 35.648 | 2.5165 | 89 | 1.8 | 1048 | 2.6 |
| 37.691 | 2.3846 | 129 | 2.6 | 1962 | 4.9 |
| 39.205 | 2.2959 | 63 | 1.3 | 513 | 1.3 |
| 39.683 | 2.2694 | 71 | 1.4 | 508 | 1.3 |

What is claimed is:

1. A method of preparing a pamoate salt of donepezil comprising
   mixing donepezil with pamoic acid in a solvent, or
   mixing a donepezil salt with a pamoate salt in a solvent.

2. The method of claim 1, wherein the pamoate salt of donepezil is amorphous or crystalline including anhydrous, hydrate, or solvate forms, and their polymorphs.

3. The method of claim 1, wherein the donepezil salt is a hydrochloride salt.

4. The method of claim 1, wherein the pamoate salt is disodium pamoate.

5. The method of claim 1, wherein the solvent is water, ethanol, or DMSO.

6. The method of claim 1, wherein the method comprises mixing donepezil with pamoic acid in DMSO.

7. The method of claim 1, wherein the method comprises mixing a donepezil salt with a pamoate salt in water or ethanol.

8. The method of claim 7, wherein the mixing comprises adding a solution of the pamoate salt in the solvent to a solution of the donepezil salt in the solvent.

9. The method of claim 2, wherein the donepezil and the pamoic acid or the donepezil salt and the pamoate salt are at a molar ratio of at least 1:1.

10. The method of claim 9, wherein the molar ratio is 1:1 or 2:1.

11. The method of claim 1, further comprising stirring for a period of time of at least 3 hours.

12. The method of claim 1, further comprising precipitating the pamoate salt of donepezil by evaporation, addition of an anti-solvent, cooling, addition of water or a combination thereof.

13. The method of claim 1, further comprising filtering and drying a precipitated pamoate salt of donepezil.

14. The method of claim 1, wherein the pamoate salt of donepezil is characterized by a powder X-ray diffraction pattern having peaks expressed as 2-theta at about 21.1, 22.4, and 24.5±0.2 degrees 2-theta, a powder X-ray diffraction pattern having peaks expressed as 2-theta at about 12.2, 19.2, 21.3 and 23.3±0.2 degrees 2-theta, a powder X-ray diffraction pattern having peaks expressed as 2-theta at about 11.6, 12.3, 18.8, 19.3, 23.3, 24.6 and 27.3±0.2 degrees 2-theta or a powder X-ray diffraction pattern having peaks expressed as 2-theta at about 9.4, 14.8, and 17.8, 22.0 and 22.3±0.2 degrees 2-theta.

\* \* \* \* \*

UNITED STATES PATENT AND TRADEMARK OFFICE
CERTIFICATE OF CORRECTION

PATENT NO. : 10,952,958 B2
APPLICATION NO. : 16/669679
DATED : March 23, 2021
INVENTOR(S) : Zi-Qiang Gu Page 1 of 1

It is certified that error appears in the above-identified patent and that said Letters Patent is hereby corrected as shown below:

In the Claims

Claim 9, Column 18, Line 35 reads:
"The method of claim 2, wherein the donepezil and the"
Whereas it should read:
"The method of claim 1, wherein the donepezil and the"

Signed and Sealed this
Sixteenth Day of August, 2022

Katherine Kelly Vidal
*Director of the United States Patent and Trademark Office*